United States Patent [19]

German et al.

[11] Patent Number: 5,885,971
[45] Date of Patent: *Mar. 23, 1999

[54] GENE THERAPY BY SECRETORY GLAND EXPRESSION

[75] Inventors: Michael German, San Francisco; Ira D. Goldfine, Kentfield; Stephen S. Rothman, Berkeley, all of Calif.

[73] Assignee: The Regents of the University of California, Oakland, Calif.

[ * ] Notice: The term of this patent shall not extend beyond the expiration date of Pat. No. 5,837,693.

[21] Appl. No.: 591,197

[22] Filed: Jan. 16, 1996

Related U.S. Application Data

[63] Continuation-in-part of Ser. No. 410,660, Mar. 24, 1995.
[51] Int. Cl.$^6$ .................................................. A61K 48/00
[52] U.S. Cl. ............................................................... 514/44
[58] Field of Search ........................... 435/240.2, 320.1; 536/23.5; 424/93.21; 514/44

[56] References Cited

U.S. PATENT DOCUMENTS

| | | |
|---|---|---|
| 4,394,443 | 7/1983 | Weissman et al. .......................... 435/6 |
| 4,683,195 | 7/1987 | Mullis et al. .............................. 435/6 |
| 4,683,202 | 7/1987 | Mullis ...................................... 435/91 |
| 4,703,008 | 10/1987 | Lin ...................................... 435/240.2 |
| 4,861,719 | 8/1989 | Miller ...................................... 435/236 |
| 5,139,941 | 8/1992 | Muzyczka et al. .................... 435/172.3 |
| 5,219,740 | 6/1993 | Miller et al. ............................ 435/69.6 |
| 5,240,846 | 8/1993 | Collins et al. ....................... 435/240.1 |
| 5,292,662 | 3/1994 | Sandmeyer .......................... 435/320.1 |
| 5,328,470 | 7/1994 | Nabel et al. ............................ 604/101 |
| 5,356,806 | 10/1994 | Harris et al. ......................... 435/240.2 |
| 5,399,346 | 3/1995 | Anderson et al. .................... 424/93.21 |
| 5,589,466 | 12/1996 | Felgner et al. ............................ 514/44 |

FOREIGN PATENT DOCUMENTS

WO 94/26915  11/1994  WIPO.

OTHER PUBLICATIONS

C Stewart et al (1993) Journal of Molecular Endocrinology 11: 335–341.
K Kozarsky et al (1993) Somatic Cell and Molecular Genetics 19: 449–458.
E. Marshall (1995) Science 269:1050–1055.
Vile et al (1995) Targeted Gene Therapy 9: 190–199.
Orkin et al (1995) Report and Recommendations of the panel to assess the NIH investment in research on gene therapy, Dec. 7.
Baum, B.J., "Advances in Salivary and Soft Tissue Management", *JADA* 125:26s–30s (1994).
Brody, S.I. and Crystal, R.G., "Adenovirus–Mediated in Vivo Gene Transfer", *N.Y. Acad. Sci.* 716:90–101 (1994).
Coghlan, A., "Gene Dream Fades Away," New Scientist, Nov. 1995:14–15.
Crystal, R.G., "Transffer of Genes to Humans: Early Lessons and Obstacles to Success," Science, 1995, vol. 270:404–410.

Grendell, J.H. and Rothman, S.S., "Effect of changes in circulating amylase levels on amylase output in bile", *The American Physiological Society* G54–G59 (1982).
Gunzburg et al., Molecular Medicine Today, 1995:410–417.
Ledley, Human Gene Therapy, 1995, 6:1129–1144.
Maeda, H., et al., "Adenovirus–Mediated Transfer of Human Lipase Complementary DNA to the Gallbladder", *Gastroentrerology* 106:1638–1644 (1994).
Marshall, "Less Hype, Mor Biology Needed for Gene Therapy," Science, Dec. 1995, vol. 270: 1751.
Mastrangeli, A. et al. 1994. "Direct in vivo adenovirus–mediated gene transfer to salivary glands." *Am. J. Physiol.* 266(6, part 1):G1146–55.
Mastrangelo et al., "Gene Therapy for Human Cancer: An Essay for Clinicians," Seminars in Oncology, vol. 23, 1:4–21, 1996.
Miyasaka, K., and Rothman, S., "Endocrine secretion of α–amylase by the pancreas", *American Physiological Society* G170–G175 (1981).
Mulligan, R.C., "The Basic Science of Gene Therapy", *Science* 260:926–932 (1993).
Newgard, C.B. et al., "Molecular engineering of the pancreatic β–cell", *J. Lab. Clin. Med.* 122(4):356–363 (1993).
Ramakrishna, J. and Grand, R.J., "Gene Therapy for Exocrine Pancreatic Insufficiency", *Gastroenterology* 106(6):1711–1713 (1994).
Samara, G. et al., "Molecular Biology and Therapy of Disease", *The American Journal of Surgery* 165:720–727 (1993).
Stewart et al., "Insulin–releasing Pituitary Cells As a Model for Somatic Cell Genen Therapy in Diabetes Mellitus", 1994, *Journal of Endocrinology*, Vol. 143, pp. 339–343.
Suggs et al., "Use of synthetic oligonucleotides as hybridization probes: Isolation of cloned cDNA sequences for human $β_2$–microglobulin," *Proc. Natl. Acad. Sci. U.S.A.* 78:6613–6617, 1981.
Gorman, et al., "The Rous sarcoma virus long terminal repeat is a strong promoter when introduced into a variety of eukaryotic cells by DNA–mediated transfection," *Proc. Natl. Acad. Sci. U.S.A.*, 79:6777–6781, 1982.
Gitschier et al., "Characterization of the human factor VIII gene," *Nature,* 312:326–330, 1984.

(List continued on next page.)

*Primary Examiner*—Bruce R. Campell
*Attorney, Agent, or Firm*—Carol L. Francis; Bozicevic & Reed LLP

[57] ABSTRACT

Secretory gland cells, particularly pancreatic and salivary gland cells, are genetically altered to operatively incorporate a gene which expresses a protein which has a desired therapeutic effect on a mammalian subject. The expressed protein is secreted directly into the gastrointestinal tract and/or blood stream to obtain therapeutic blood levels of the protein thereby treating the patient in need of the protein. The transformed secretory gland cells provide long term therapeutic cures for diseases associated with a deficiency in a particular protein or which are amenable to treatment by overexpression of a protein.

11 Claims, 10 Drawing Sheets

OTHER PUBLICATIONS

Yang et al., "In vivo and in vitro gene transfer to mammalian somatic cells by particle bombardmnt," *Proc. Natl. Acad. Sci. U.S.A.*, 87:9568–9572, 1990.

Kwano, et al., "Complete Nucleotide Sequence of the Matrix Gene of Human Parainfluenza Type 2 Virus and Expression of the M Protein in Bacteria," *Virol.*, 179:857–861, 1990.

Wolff et al., "Direct Gene Transfer into Mouse Muscle in Vivo,"*Science*, 247:1465–1468, 1990.

Hewitt et al., "Human Gastric Intrinsic Factor: Characterization of cDNA and Genomic Clones and Localization to Human Chromosome 11," *Genomics*, 10:432–440, 1991.

Rosenfeld et al., "Adenovirus–Mediated Transfer of a Recombinant α1–Antitrypsin Gene to the Lung Epithelium in Vivo,"*Science*, 252:431–434, 1991.

Rosenfeld et al., "In Vivo Transfer of the Human Cystic Fibrosis Transmembrane Conductance Regulator Gene to the Airway Epithelium," *Cell*, 68:143–155, 1992.

Robins et al., "Retrotransposons and the evolution of mammalian gene expression," *Genetica*, 86:191–201, 1992.

Ting et al., "Endogenous retroviral sequences are required for tissue–specific expression of human salivary amylase gene," *Genes Dev.*, 6:1457–65, 1992.

Tanabayashi et al., "Expression of Mumps Virus Glycoproteins in Mammalian Cells from Cloned cDNAs: Both F and HN Proteins Are Required for Cell Fusion," *Virol.*, 187:801–804, 1992.

Takeuchi et al., "In vitro transcription and replication of the mumps virus genome," *Archiv. Virol.*, 128:177–183, 1993.

Tanabayashi et al., "Identification of an Amino Acid That Defines the Fusogenicity of Mumps Virus," *J. Virol.*, 67:2928–2931, 1993.

Gerrard et al., "Towards gene therapy for haemophilia B using primary human keratinocytes," *Nat. Genet.*, 3:180, 1993.

Fynan et al., "DNA vaccines: Protective immunizations by parenteral, mucosal, and gene–gun inoculations," *Proc. Natl. Acad. Sci. U.S.A.*, 90:11478–11482, 1993.

Morsy et al., "Progress Toward Human Gene Therapy," *JAMA*, 270:2338–2345, 1993.

Wood, et al., "Expression of active human factor VIII from recombinant DNA clones," *Nature*, 312:330–337, 1984.

Boshart et al., "A Very Strong Enhancer is Located Upstream of an Immediate Early Gene of Human Cytomegalovirus," *Cell*, 41:521–530, 1985.

Hagenbuchle et al., "Expression of Mouse Amy–$2^a$ Alpha–amylase Genes is Regulated by Strong Pancreas-specific Promoters," *J. Mol. Biol.*, 185:285–293, 1985.

Pittet et al., "Mouse Alpha–amylase Loci, Amy–$1^a$ and Amy–$2^a$, are Closely Linked," *J. Mol. Biol.*, 182:359–365, 1985.

Schibler et al., "Structural arrangement and tissue–specific expression of the two murine alpha–amylase loci Amy–1 and Amy–2," *Oxf. Surv. Eukaryot. Genes*, 3:210–234, 1986.

Morgan et al., "Expression of an Exogenous Growth Hormone Gene by Transplantable Human Epidermal Cells," *Science*, 237:1476–1479, 1987.

Korman et al., "Expression of human class II major histocompatibility complex antigens using retrovirus vectors," *Proc. Natl. Acad. Sci. U.S.A.*, 84:2150–2154, 1987.

Felgner et al., "Lipofection: A highly efficient, lipid–mediated DNA–transfection procedure," *Proc. Natl. Acad. Sci. U.S.A.*, 84:7413–7417, 1987.

Samuelson et al., "Expression of the human amylase genes: recent origin of a salivary amylase promoter from an actin pseudogene," *Nucleic Acids Res.* 16:8261–8276, 1988.

Elango et al., "Molecular Cloning and Characterization of Six Genes, Determination of Gene Order and Intergenic Sequences and Leader Sequence of Mumps Virus," *J. Gen. Virol.*, 69:2893–2900, 1988.

Tomita et al., "A novel type of human α–amylase produced in lung carcinoid tumor," *Gene*, 76:11–18, 1989.

Cockell et al., "Identification of a Cell–Specific DNA–Binding Activity That Interacts with a Transcriptional Activator of Genes Expressed in the Acinar Pancreas," *Mol. Cell. Biol.*, 9:2464–2476, 1989.

Groot et al., "The Human α–Amylase Multigene Family Consists of Haplotypes with Variable Numbers of Genes," *Genomics*, 5:29–42, 1989.

Avery et al., "Studies on the Chemical Nature of the Substance Inducing Transformation of Pneumococcal Types," *J. Exp. Med.*, 79:137–158, 1944.

Lowry et al., "Protein Measurement With the Folin Phenol Reagent," *J. Biol. Chem.* 193:265–275, 1951.

Amsterdam et al., "Studies on Dispersed Pancreatic Exocrine Cells," *J. Cell. Biol.* 63:1057–1073, 1974.

Towbin et al., "Electrophoretic Transfer of Proteins From Polyacrylamide Gels to Nitrocellulose Sheets: Procedure and Some Applications," *Proc. Natl. Acad. Sci. USA* 76:4350–4354, 1979.

Sierra et al., "Different Tissue–Specific Expression of the Amylase Gene *Amy–1* in Mice and Rats," *Mol. Cell. Biol.* 6(11):4067–4076, 1986.

Martial et al., "Human Growth Hormone: Complementary DNA Cloning and Expression in Bacteria," *Biotechnology* 24:293–298, 1992.

Jones et al., "A Salivary Amylase Transgene is Efficiently Expressed in Liver but Not in Parotid Gland of Transgenic Mice," *Nucleic Acids Res.* 17(6):6613–6623, 1989.

GENE THERAPY BY SECRETORY GLAND EXPRESSION

This application is a continuation-in-part of U.S. application Ser. No. 08/410,660, filed Mar. 24, 1995.

FIELD OF THE INVENTION

This invention relates generally to the field of gene therapy and more particularly to the application of gene therapy to the cells of a secretory gland.

BACKGROUND OF THE INVENTION

Although gene therapy and specifically human gene therapy has been widely discussed only over the last five years, the basic idea first became a reality in 1944 when Avery et al. carried out research on the chemical nature of substances inducing transformation of pneumococcal types. (Avery et al., *J. Exp. Med.* 79:137–158, 1944). The work carried out by Avery et al., did not involve the actual insertion of genetic material into cells in order to carry out gene therapy. The insertion of new genetic material into cells in order to permanently affect the genetic makeup of the cells is the methodology now generally referred to as gene therapy.

Current gene therapy is carried out in a variety of ways but involves two general protocols. In the first method, referred to as ex vivo gene therapy, cells are extracted from an organism such as a human and subsequently subjected to genetic manipulation by a variety of different means. After genetic material has been properly inserted into the cells, the cells are implanted back into the body from which they were removed. Thus the process involves cell removal, transformation of the cells in vitro, and subsequent reintroduction of the modified cells into the patient. Persistent, in vivo expression of the newly implanted genetic material after transplantation of the transformed cells has been successful (see Morgan et al., *Science* 237:1476 (1987); and Gerrard et al., *Nat. Genet.* 3:180 (1993)).

In the second approach to gene therapy, referred to as in vivo gene therapy, somatic cells within a living organism are transformed with new genetic material. For example, the genetic material to be introduced into the organism is packaged within a retrovirus or adenovirus. The virus containing the desired genetic material is allowed to infect target cells within the organism. Upon infection of the cells, the virus injects genetic material into the cells which is then integrated into the cells' genome. As a result, the injected genetic material is expressed and the patient is treated.

Several different methods for transforming cells can be used in accordance with either the ex vivo or in vivo transfection procedures. For example, various mechanical methods can be used to deliver the genetic material, including the use of fusogenic lipid vesicles (liposomes incorporating cationic lipids such as lipofection; see Felgner et al., *Proc. Natl. Acad. Sci. U.S.A.* 84:7413–7417 (1987)); direct injection of DNA (Wolff, et al., *Science* (1990) 247:1465–1468); and pneumatic delivery of DNA-coated gold particles with a device referred to as the gene gun (Yang et al., *Proc. Natl. Acad. Sci. U.S.A.* 1990; 87:1568–9572).

Ex vivo and in vivo gene transfer methodologies have been accomplished using a variety of different procedures, such as the use of retroviruses or direct injection. The procedures have been used on five general types of cells in order to carry out (1) liver cell gene therapy; (2) hematopoietic cell gene therapy; (3) cancer cell gene therapy; (4) respiratory cell gene therapy; and (5) muscle cell gene therapy. A review of the different techniques along with a citation of numerous publications in each area is contained within a recent article on human gene therapy (see Morsy et al., *JAMA* 270:2338–2345 (1993)).

Depending on the desired result, the effect which the inserted genetic material will have on the transformed cell can vary greatly and can be selected according to the specific therapeutic situation. For example, genetic material inserted into the cells in order to obtain circulation of the expressed genetic products would not be used in connection with the treatment of cancer cells of a localized tumor. Stated differently, gene therapy may be carried out in order to locally affect a given type of cells such as affecting cancer cells within a tumor or locally affecting liver cells. Other types of gene therapy are carried out in order to cause the manipulated cells to express a protein which is transported to the circulatory system and systemically delivered to the organism. Genetic manipulation of cells to express a protein for systemic delivery to the organism has been problematic. The present invention addresses this problem.

SUMMARY OF THE INVENTION

Secretory gland cells are genetically altered to operatively incorporate a gene which expresses a therapeutically effective protein. More particularly, cells of a salivary gland or the pancreas are genetically altered to operatively incorporate DNA which when expressed produces a protein which has a desired therapeutic effect on the patient. The expressed protein is secreted directly into the blood stream and/or into the gastrointestinal system to obtain therapeutic levels of the protein, thereby treating the patient in need of the protein.

A primary object is to provide a method of gene therapy wherein cells of a secretory gland, preferably the pancreas or a salivary gland, more preferably a parotid gland, of a mammal are genetically modified to express a biologically active and therapeutically useful protein which protein is secreted into the circulatory system and/or the gastrointestinal tract of the individual.

Another object is to produce genetically transformed secretory gland cells which cells have incorporated into their genome genetic material which expresses a biologically active and therapeutically useful protein and secretes that protein into the surrounding media.

An advantage of the present invention is that long term therapeutic cures can be provided for diseases wherein individuals are suffering from the disease due to a deficiency in a particular protein.

A feature of the present invention is that cells of a secretory gland, preferably the pancreas or a salivary gland, more preferably a parotid gland, are specifically targeted.

Another advantage of the present invention is that the expressed protein is secreted into the circulatory system and saliva or pancreatic juices of the patient to provide a systemic effect.

These and other objects, advantages and features of the present invention will become apparent to those persons skilled in the art upon reading the details of the vectors, cell lines and methodology as more fully set forth below.

DESCRIPTION OF THE PREFERRED EMBODIMENTS

Figure 1:
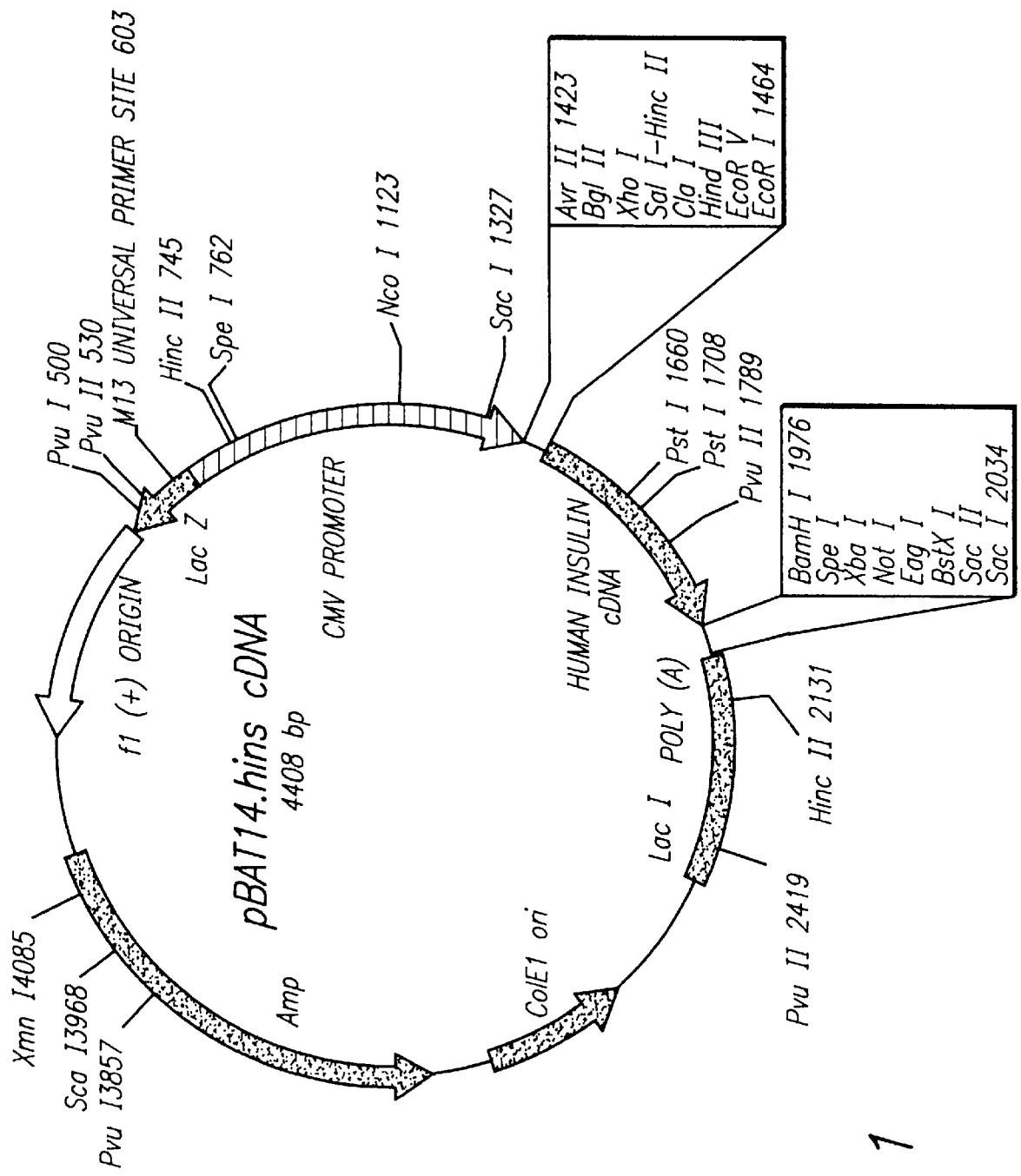
FIG. 1 is a schematic view of a recombinant plasmid construct useful in producing recombinant salivary gland cells of the invention.
Figure 2:
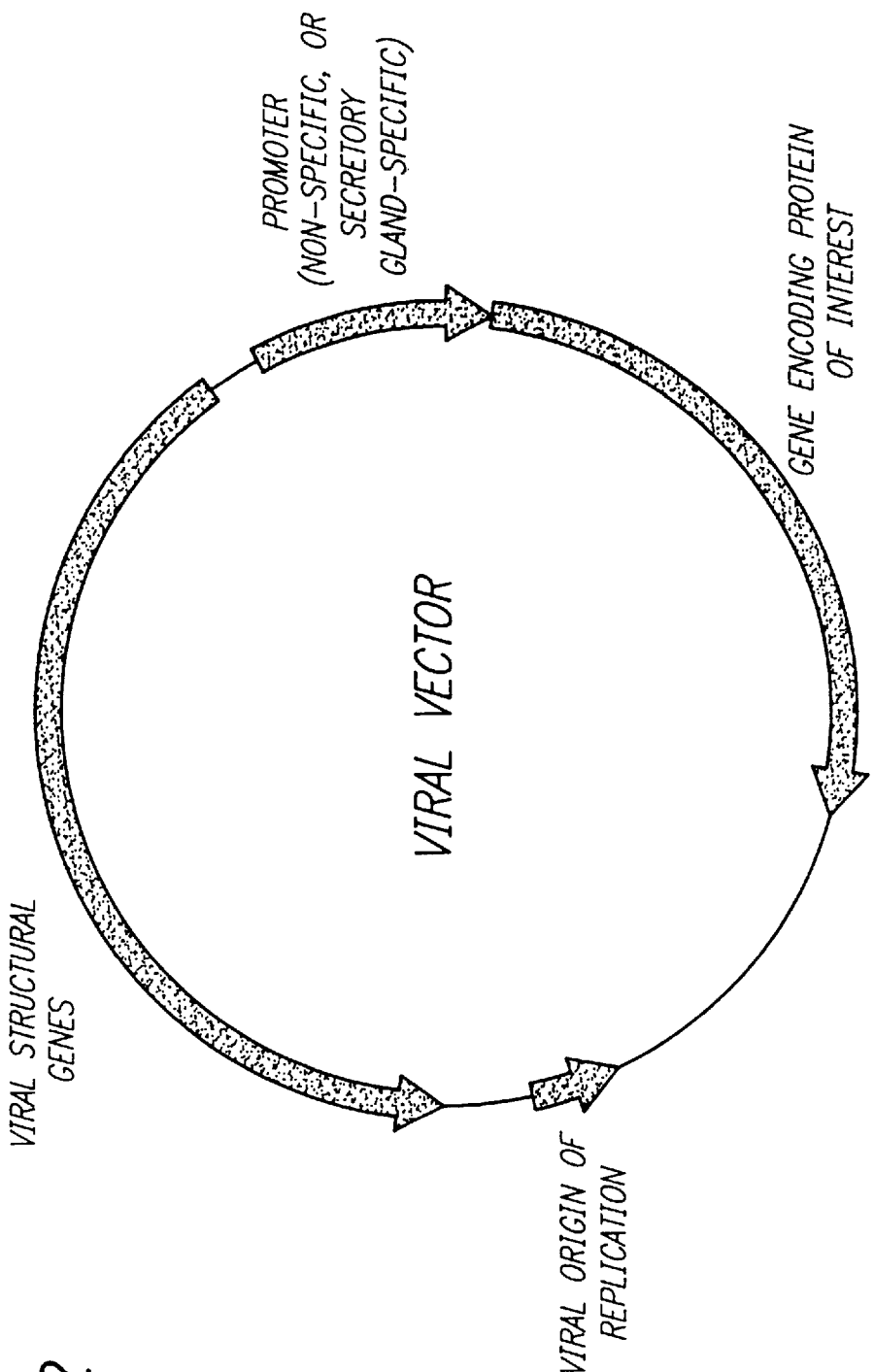
FIG. 2 is a schematic view of a recombinant viral construct useful in producing recombinant secretory gland cells of the invention.

Before the present method of genetically transforming secretory gland cells and methods for providing gene therapy are described, it is to be understood that this invention is not limited to the particular methodology, protocols, cell lines, secretory glands, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a secretory gland cell" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention.

Definitions

By "secretory gland" is meant an aggregation of cells specialized to secrete or excrete materials not related to their ordinary metabolic needs. Secretory glands include salivary glands, pancreas, mammary glands, thyroid gland, thymus gland, pituitary gland, liver, and other glands well known in the art.

By "salivary gland" is meant a gland of the oral cavity which secretes saliva, including the glandulae salivariae majores of the oral cavity (the parotid, sublingual, and submandibular glands) and the glandulae salivariae minores of the tongue, lips, cheeks, and palate (labial, buccal, molar, palatine, lingual, and anterior lingual glands).

By "pancreas" is meant a large, elongated, racemose gland situated transversely behind the stomach, between the spleen and the duodenum. The pancreas is composed of an endocrine portion (the pars endocrina) and an exocrine portion (the pars exocrina). The pars endocrina, which contains the islets of Langerhans, produces and secretes proteins, including insulin, directly into the blood stream. The pars exocrina contains secretory units and produces and secretes a pancreatic juice, which contains enzymes essential to protein digestion, into the duodenum.

By "transformation" is meant a permanent genetic change induced in a cell following incorporation of new DNA (i.e., DNA exogenous to the cell). Where the cell is a mammalian cell, the permanent genetic change is generally achieved by introduction of the DNA into the genome of the cell.

By "transfection" is meant the transformation of a cell with DNA from a virus.

By "transformed cell" is meant a cell into which (or into an ancestor of which) has been introduced, by means of recombinant DNA techniques, a DNA molecule encoding a protein of interest.

By "DNA of interest" is meant any DNA sequence which encodes a protein or other molecule which is desirable for administration, particularly intravenous administration, to a mammalian subject by gene therapy the sequence is generally operatively linked to other sequences which are needed for its expression such as a promoter.

By "vector" is meant any compound, biological or chemical, which facilitates transformation of a target cell (e.g., a secretory gland cell) with a DNA of interest. Exemplary biological vectors include viruses, particularly attenuated and/or replication-deficient viruses. Exemplary chemical vectors include lipid complexes and naked DNA constructs.

By "promoter" is meant a minimal DNA sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

By "secretory gland specific promoter" is meant a promoter which directs expression of an operably linked DNA sequence when bound by transcriptional activator proteins, or other regulators of transcription, which are unique to a specific type of secretory gland cell. For example, by "salivary gland specific promoter" is meant a secretory gland specific promoter which directs expression in a salivary gland cell. A salivary amylase promoter is an example of a salivary gland specific promoter. By "pancreas specific promoter" is meant a secretory gland specific promoter which directs expression in a pancreatic cell. Examples of pancreas specific promoters include a pancreatic amylase promoter and an insulin promoter.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that the DNA of interest introduced into the cell is positioned adjacent a DNA sequence which directs transcription and translation of the introduced DNA (i.e., facilitates the production of, e.g., a polypeptide encoded by a DNA of interest).

By "mammalian subject" or "mammalian patient" is meant any mammal for which gene therapy is desired, including human, bovine, equine, canine, and feline subjects.

The present invention features compositions and methods of treatment using gene therapy, more specifically gene therapy by expression of a DNA of interest in cells within a secretory gland of a mammalian patient. Preferably, the transformed secretory gland cells expressing the protein encoded by the DNA of interest secrete a therapeutically effective amount of the protein into the blood stream or into the gastrointestinal tract (e.g., into the saliva or pancreatic juices) of the mammalian patient. Preferably, the secretory gland into which the DNA of interest is introduced and expressed is the pancreas, more preferably a salivary gland, even more preferably the parotid gland. Preferably, the DNA of interest encodes either insulin, a growth hormone, clotting factor VIII, intrinsic factor, or erythropoietin. Preferably, the DNA of interest is operably linked to a secretory gland-specific promoter. Where the secretory gland is the pancreas, the promoter is preferably a pancreatic amylase promoter or an insulin promoter. Where the secretory gland is a salivary gland, the promoter is preferably a salivary amylase promoter.

The invention also features recombinant secretory gland cells, preferably recombinant pancreatic or recombinant salivary gland cells, more preferably recombinant parotid gland cells, containing a DNA of interest operatively inserted in the genome of the cell and operatively linked to a promoter for expression of the DNA of interest. Preferably, the promoter operatively linked to the DNA of interest is a secretory gland specific promoter. Where the secretory gland is the pancreas, the promoter is preferably a pancreatic amylase promoter or insulin promoter. Where the secretory gland is a salivary gland, the promoter is preferably a salivary amylase promoter.

The invention will now be described in further detail.
Vectors and Constructs

Any nucleic acid vector having a eukaryotic promoter operably linked to a DNA of interest can be used in the invention to transform a secretory gland cell. The vectors containing the DNA sequence (or the corresponding RNA sequence) which may be used in accordance with the invention may be any eukaryotic expression vector containing the DNA or the RNA sequence of interest. For example, a plasmid or viral vector (e.g. adenovirus) can be cleaved to provide linear DNA having ligatable termini. These termini are bound to exogenous DNA having complementary, like ligatable termini to provide a biologically functional recombinant DNA molecule having an intact replicon and a desired phenotypic property.

A variety of techniques are available for DNA recombination in which adjoining ends of separate DNA fragments are tailored to facilitate ligation. The exogenous (i.e., donor) DNA used in the invention is obtained from suitable cells. The vector is constructed using known techniques to obtain a transformed cell capable of in vivo expression of the therapeutic protein. The transformed cell is obtained by contacting a target cell with a RNA- or DNA-containing formulation permitting transfer and uptake of the RNA or DNA into the target cell. Such formulations include, for example, viruses, plasmids, liposomal formulations, or plasmids complexed with polycationic substances such as poly-L-lysine or DEAC-dextran, and targeting ligands.

Techniques for obtaining expression of exogenous DNA or RNA sequences in a host are known in the art (see, for example, Kormal et al., *Proc. Natl. Acad. Sci. USA*, 84:2150–2154, 1987; Sambrook et al. *Molecular Cloning: A Laboratory Manual*, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Various vectors (e.g., viral vectors, bacterial vectors, or vectors capable of replication in eukaryotic and prokaryotic hosts) can be used in accordance with the present invention. Preferably the vector is capable of replication in both eukaryotic and prokaryotic hosts. Numerous vectors which can replicate in eukaryotic and prokaryotic hosts are known in the art and are commercially available. In general, such vectors used in accordance with the invention are composed of a bacterial origin of replication and a eukaryotic promoter operably linked to a DNA of interest.

In general, viral vectors used in accordance with the invention are composed of a viral particle derived from a naturally-occurring virus which has been genetically altered to render the virus replication-defective and to express a recombinant gene of interest in accordance with the invention. FIG. 3 shows a schematic view of an exemplary recombinant vector construct useful in the method of the invention. Once the virus delivers its genetic material to a cell, it does not generate additional infectious virus but does introduce exogenous recombinant genes into the cell, preferably into the genome of the cell.

Numerous viral vectors are well known in the art, including, for example, retrovirus, adenovirus, adeno-associated virus, herpes simplex virus (HSV), cytomegalovirus (CMV), vaccinia and poliovirus vectors. Retroviral vectors are less preferred since retroviruses require replicating cells and secretory glands are composed of mostly slowly replicating and/or terminally differentiated cells. Adenovirus is a preferred viral vector since this virus efficiently infects slowly replicating and/or terminally differentiated cells. Where the secretory gland is a salivary gland, the viral vector is preferably derived from an attenuated and/or replication-deficient mumps virus or other attenuated and/or replication-deficient virus which is substantially specific for salivary gland cells.

Where a replication-deficient virus is used as the viral vector, the production of infective virus particles containing either DNA or RNA corresponding to the DNA of interest can be produced by introducing the viral construct into a recombinant cell line which provides the missing components essential for viral replication in trans. Preferably, transformation of the recombinant cell line with the recombinant viral vector will not result in production of replication-competent viruses, e.g., by homologous recombination of the viral sequences of the recombinant cell line into the introduced viral vector.

Methods for production of replication-deficient viral particles containing a DNA of interest are well known in the art and are described in, for example, Rosenfeld et al., *Science* 252:431–434, 1991 and Rosenfeld et al., *Cell* 68:143–155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and entire sequence of the mumps viral genome are described in Tanabayashi et al., *J. Virol.* 67:2928–2931, 1993; Takeuchi et al., *Archiv. Virol.*, 128:177–183, 1993; Tanabayashi et al., *Virol.* 187:801–804, 1992; Kawano et al., *Virol.*, 179:857–861, 1990; Elango et al., *J. Gen. Virol.*

69:2893–28900, 1988. Given the knowledge in the art regarding the mumps viral genome and the genes important for mumps virus fusion and replication, mumps viral vectors can be readily constructed, and replication defective mumps virus strains developed, for use in salivary gland specific gene transfer, gene expression and gene therapy.

The DNA of interest may be administered using a non-viral vector, for example, as a DNA- or RNA-liposome complex formulation. Such complexes comprise a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-β-ol 3-urethanyl)-N',N'-dimethylethylene diamine). When the DNA of interest is introduced using a liposome, it is preferable to first determine in vitro the optimal values for the DNA:lipid ratios and the absolute concentrations of DNA and lipid as a function of cell death and transformation efficiency for the particular type of cell to be transformed. These values can then be used in or extrapolated for use in in vivo transformation. The in vitro determinations of these values can be readily carried out using techniques which are well known in the art.

Other non-viral vectors may also be used in accordance with the present invention. These include chemical formulations of DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted secretory gland or receptor ligands, i.e., molecules capable of interacting with receptors associated with a cell of a targeted secretory gland.

Preferably, the DNA construct contains a promoter to facilitate expression of the DNA of interest within a secretory gland cell, more preferably a pancreatic cell or salivary gland cell, even more preferably a parotid gland cell. Preferably the promoter is a strong, eukaryotic promoter. Exemplary eukaryotic promoters include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., *Cell* 41:521–530, 1985) and the promoter from the long terminal repeat (LTR) of RSV (Gorman et al., *Proc. Natl. Acad. Sci. USA* 79:6777–6781, 1982). Of these two promoters, the CMV promoter is preferred as it provides for higher levels of expression than the RSV promoter.

Where the secretory gland is the pancreas, the promoter used in the vector is preferably a pancreas specific promoter, i.e. the promoter facilitates specific expression of the DNA to which it is operably linked when the construct is in the presence of a pancreas cell specific transcriptional activator protein. The promoters may be derived from the genome of any mammal, and is preferably derived from a murine or a human source, more preferably from a human source. Examples of preferred pancreas specific promoters include the insulin promoter and pancreas α-amylase promoters.

Where the secretory gland is a salivary gland, the promoter used in the vector is preferably a salivary gland specific promoter, i.e. the promoter facilitates specific expression of the DNA to which it is operably linked when the construct is in the presence of a salivary gland cell specific transcriptional activator protein(s). Examples of preferred salivary gland specific promoters include salivary α-amylase promoters and mumps viral gene promoters which are specifically expressed in salivary gland cells.

Multiple pancreatic α-amylase genes and multiple salivary α-amylase genes, have been identified and characterized in both mice and humans (see, for example, Jones et al., *Nucleic Acids Res.*, 17:6613–6623; Pittet et al., *J. Mol. Biol.*, 182:359–365, 1985; Hagenbuchle et al., *J. Mol. Biol.*, 185:285–293, 1985; Schibler et al., *Oxf. Surv. Eukaryot. Genes*, 3:210–234, 1986; and Sierra et al., *Mol. Cell. Biol.*, 6:4067–4076, 1986 for murine pancreatic and salivary α-amylase genes and promoters; Samuelson et al., *Nucleic Acids Res.*, 16:8261–8276, 1988; Groot et al., *Genomics*, 5:29–42, 1989; and Tomita et al., *Gene*, 76:11–18, 1989 for human pancreatic and salivary α-amylase genes and their promoters). The promoters of these α-amylase genes direct either pancreas or salivary gland specific expression of their corresponding α-amylase encoding DNAs. These promoters may thus be used in the constructs of the invention to achieve pancreas-specific or salivary gland-specific expression of a DNA of interest.

For example, the human genome contains three, nearly identical salivary α-amylase genes, termed AMY1A, AMY1B, and AMY1C, as well as at least two pancreatic α-amylase genes. The promoters of three salivary α-amylase genes appear identical. The region from −1003 to −327 base pairs of the human salivary α-amylase AMY1C promoter sequence is sufficient for parotid gland specific expression, while the region from −1003 to −826 is necessary for salivary gland specific expression (Ting et al., *Genes Dev.* 6:1457–65, 1992). This human salivary promoter sequence can be operably linked to a DNA of interest in a construct for salivary-gland specific expression according to the present invention.

Recombinant promoters derived from any of the above-described promoters may also be employed in constructs to achieve secretory gland specific expression of a specific gene of interest. For example, a recombinant promoter capable of directing expression at increased levels relative to a wild-type salivary α-amylase promoter may be produced by multimerizing the −1003 to −826 region of the salivary α-amylase promoter in the construct, or by operably linking a viral enhancer sequence (e.g., an enhancer sequence from CMV) to a full length salivary α-amylase promoter sequence.

The constructs of the invention may also include sequences in addition to promoters which enhance secretory gland specific expression. For example, where pancreas specific expression of the DNA of interest is desired, the construct may include a PTF-1 recognition sequence (Cockell et al., *Mol. Cell. Biol.*, 9:2464–2476, 1989). Sequences which enhance salivary gland specific expression are also well known in the art (see, for example, Robins et al., *Genetica* 86:191–201, 1992).

Other components such as a marker (e.g., an antibiotic resistance gene (such as an ampicillin resistance gene) or β-galactosidase) to aid in selection of cells containing and/or expressing the construct, an origin of replication for stable replication of the construct in a bacterial cell (preferably, a high copy number origin of replication), a nuclear localization signal, or other elements which facilitate production of the DNA construct, the protein encoded thereby, or both.

For eukaryotic expression (e.g., in a salivary gland cell), the construct should contain at a minimum a eukaryotic promoter operably linked to a DNA of interest, which is in turn operably linked to a polyadenylation sequence. The polyadenylation signal sequence may be selected from any of a variety of polyadenylation signal sequences known in the art. Preferably, the polyadenylation signal sequence is the SV40 early polyadenylation signal sequence. The construct may also include one or more introns, which can increase levels of expression of the DNA of interest, particularly where the DNA of interest is a cDNA (e.g., contains no introns of the naturally-occurring sequence). Any of a variety of introns known in the art may be used. Preferably, the intron is the human β-globin intron and inserted in the construct at a position 5' to the DNA of interest.

The DNA of interest can be any DNA encoding any protein for which intravenous therapy and/or therapy for the gastrointestinal tract is desirable. For example, intravenous protein therapy is appropriate in treating a mammalian subject having an inherited or acquired disease associated with a specific protein deficiency (e.g., diabetes, hemophilia, anemia, severe combined immunodeficiency). Such protein deficient states are amenable to treatment by replacement therapy, i.e., expression of a protein to restore the normal blood stream levels of the protein to at least normal levels. Secretion of a therapeutic protein to the gastrointestinal tract (e.g. by secretion of the protein into the saliva, pancreatic juices, or other mucosal secretion) is appropriate where, for example, the subject suffers from a protein deficiency associated with absorption of nutrients (e.g. deficiency in intrinsic factor) or digestion (e.g., deficiencies in various pancreatic enzymes).

Alternatively, the mammalian subject may have a condition which is amenable to treatment by expression or overexpression of a protein which is either normally present in a healthy mammalian subject or is foreign to the mammalian subject. For example, intravenous protein therapy can be used in treatment of a mammalian subject having a viral (e.g., human immunodeficiency virus (HIV), Epstein-Barr virus (EBV), herpes simplex virus (HSV), bacterial, fungal, and/or parasitic infection, particularly where the infection is chronic, i.e., persisting over a relatively long period of time. The secretory gland gene therapy of the invention may also be used to enhance expression of a protein present in a normal mammal, or to express a protein not normally present in a normal mammal, in order to achieve a desired effect (e.g., to enhance a normal metabolic process). For example, a secretory gland of a dairy cow may be transformed with DNA encoding bovine growth hormone (BGH) in order to enhance levels of BGH in the blood stream and enhance milk production.

The DNA of interest is preferably obtained from a source of the same species as the mammalian subject to be treated (e.g. human to human), but this is not an absolute requirement. DNA obtained from a species different from the mammalian subject can also be used, particularly where the amino acid sequences of the proteins are highly conserved and the xenogeneic protein is not highly immunogenic so as to elicit a significant, undesirable antibody response against the protein in the mammalian host.

Exemplary, preferred DNAs of interest include DNA encoding insulin, growth hormone, clotting factor VIII, intrinsic factor, and erythropoietin. Of particular interest is intravenous protein therapy of a mammalian subject (e.g., a bovine, canine, feline, equine, or human subject, preferably a bovine or human subject, more preferably a human subject) by expression of DNA encoding a protein (e.g., insulin, growth hormone, clotting factor VIII, or erythropoietin) in a transformed mammalian salivary gland cell, preferably a mammalian parotid gland cell. Preferably, the subject is a human subject and the DNA expressed encodes a human protein (e.g., human insulin, human growth hormone, human clotting factor VIII, or human erythropoietin). Other exemplary DNAs of interest include tissue plasminogen activator (tPA), urokinase, streptokinase, acidic fibroblast growth factor, basic fibroblast growth factor, tumor necrosis factor alpha, tumor necrosis factor β, transforming growth factor β, platelet-derived growth factor, endothelian, and soluble CD4. Table 1 provides a list of exemplary proteins and protein classes which can be delivered by the secretory gland gene therapy of the invention.

TABLE 1

Exemplary Proteins and Protein Classes for Secretory Gland Gene Therapy

SPECIFIC EXEMPLARY PROTEINS

| | |
|---|---|
| insulin | interferon-α2B |
| human growth hormone (hGH) | transforming growth factor (TGF) |
| erythropoietin (EPO) | ciliary neurite transforming factor (CNTF) |
| clotting factor VIII | insulin-like growth factor-1 (IGF-1) |
| bovine growth hormone (BGH) | granulocyte macrophage colony stimulating factor (GM-CSF) |
| platelet derived growth factor (PDGF) | interferon-α2A |
| clotting factor VIII | brain-derived neurite factor (BDNF) |
| thrombopoietin (TPO) | insulintropin |
| IL-1 | tissue plasminogen activator (tPA) |
| IL-2 | urokinase |
| IL-1 RA | streptokinase |
| superoxide dismutase (SOD) | adenosine deamidase |
| catalase | calcitonin |
| fibroblast growth factor (FGF) (acidic or basic) | arginase |
| neurite growth factor (NGF) | phenylalanine ammonia lyase |
| granulocyte colony stimulating factor (G-CSF) | γ-interferon |
| L-asparaginase | pepsin |
| uricase | trypsin |
| chymotrypsin | elastase |
| carboxypeptidase | lactase |
| sucrase | intrinsic factor |
| calcitonin | parathyroid hormone(PTH)-like hormone |
| Ob gene product | cholecystokinin (CCK) |
| glucagon | insulinotrophic hormone |

EXEMPLARY CLASSES OF PROTEINS

| | |
|---|---|
| proteases | pituitary hormones |
| protease inhibitors | growth factors |
| cytokines | somatomedians |
| chemokines | immunoglobulins |
| gonadotrophins | interleukins |
| chemotactins | interferons |
| lipid-binding proteins | |

Various disease conditions are amenable to treatment using the secretory gland gene therapy of the invention. One skilled in the art can recognize the appropriate protein which should be produced by the invention for treating specific disease conditions. Exemplary diseases which are amenable to treatment using the subject invention, and exemplary, appropriate proteins which can be used in treating these diseases, are shown in Table 2.

TABLE 2

Exemplary Disease Conditions Amenable to Secretory Gland Gene Therapy

| Enzyme Deficiency | Endotoxic Shock/Sepsis |
|---|---|
| Adenosine deaminase[1] | Lipid-binding protein (LBP) |
| Purine nucleotide phosphorylase | |
| Galactosidase | |
| β-glucuronidase | |
| Antioxidants for Cancer Therapy | Anemia |
| Superoxide dismutase | Erythropoietin |
| Catalase | |
| Cancer | Growth Factors (for use in wound healing, |
| α-Interferon | induction of red blood cell formation, etc.) |
| γ-Interferon | Epidermal growth factor |
| α-IL1 | G-CSF |
| Phenylalanine ammonia lyase | γ-Interferon |
| Arginase | Transforming growth factor |
| L-asparaginase | Erythropoietin |
| Uricase | Thrombopoietin |
| Granulocyte colony stimulating factor (G-CSF) | Insulin-like growth factor-1 |
| Monoclonal antibodies | Insulin |
| Tissue necrosis factor | Human growth hormone |
| Cardiovascular Disease | Diabetes |
| Tissue plasminogen activator | Insulin |
| Urokinase (native or chimeric) | Glucagon |
| $\alpha_1$-antitrypsin | Insulinotrophic hormone |
| Antithrombin-III | |
| Other proteases or protease inhibitors | Clotting disorders |
| Apolipoproteins (particularly B-48) | Clotting factor VIII |
| Circulating Scavenger Receptor | |
| APO Al$_2$ | |
| Obesity and Feeding | Autoimmune diseases |
| Ob gene product | Intrinsic factor |
| Cholecystokinin (CCK) | (for pernicious anemia, a vitamin B$_{12}$ |
| | absorption deficiency) |
| Bone diseases | Gastrointestinal and Pancreatic Deficiencies |
| Calcitonin | Pepsin (for esophageal reflux) |
| PTH-like hormone | Trypsin |
| | Chymotrypsin |
| | Elastase |
| | Carboxypeptidase |
| | Lactase (for lactose deficiency) |
| | Sucrase |
| | Intrinsic Factor |

[1] For treatment of severe combined immunodeficiency
[2] Converts low-density lipoproteins to high-density lipoproteins Numerous proteins which are desirable for intravenous protein therapy are well known in the art and the DNA encoding these proteins has been isolated. For example, the sequence of the DNAs encoding insulin, human growth hormone, intrinsic factor, clotting factor VIII, and erythropoietin are available from Genbank and/or have been described in the scientific literature (e.g., human clotting factor VIII gene: Gitschier et al., Nature 312:326–330, 1984; Wood et al., Nature 312:330–337, 1984; human intrinsic factor: Hewitt et al., Genomics 10:432–440, 1991). Proteins commonly used in treatments can be used in the gene therapy procedures of the present invention. Such proteins are disclosed in, for example, the Physicians' Desk Reference (1994 Physicians' Desk Reference, 48th Ed., Medical Economics Data Production Co., Montvale, N.J.; incorporated by reference) and can be dosed using methods described in Harrison's Principles of Internal Medicine and/or the AMA "Drug Evaluations Annual" 1993, all incorporated by reference.

Where the DNA encoding a protein of interest has not been isolated, this can be accomplished by various, standard protocols well known to those of skill in the art (see, for example, Sambrook et al., ibid; Suggs et al., Proc. Natl. Acad. Sci. USA 78:6613–6617, 1981; U.S. Pat. No. 4,394,443; each of which are incorporated herein by reference with respect to identification and isolation of DNA encoding a protein of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (U.S. Pat. Nos. 4,683,195 and 4,683,202). Nucleotide substitutions, deletions, additions, and the like can also be incorporated into the polynucleotides, so long as the ability of the polynucleotide to hybridize is not substantially disrupted. (Sambrook et al.

ibid). The clones may be expressed or the DNA of interest can be excised or synthesized for use in other constructs. If desired, the DNA of interest can be sequenced using methods well known in the art.

In a preferred embodiment, the construct used in the present invention is designed so as to enhance protein secretion from the transformed secretory gland cell into the blood stream. Secretory gland cells are normally polarized, with the apical surface oriented toward the ductal system and the basolateral surface oriented toward the blood supply. Most proteins produced by the pancreas and salivary glands are released into the duct system and eventually into the gastrointestinal tract. However, some secretory gland proteins, such as kallikreins, are secreted primarily into the blood stream. Regardless of whether a specific secretory gland protein is primarily released into the duct system or into the blood stream, there is a modest rate of transport of these same proteins into the secondary system. Secretory gland proteins are not normally partitioned solely into the blood stream or solely into the gastrointestinal tract. For example, amylase, which is primarily secreted into the duct systems, is also released at a lower level into the blood stream.

The specific features responsible for mediating intravenous-directed or duct system-directed secretion have not been described. However, when salivary gland cells are transformed with DNA encoding insulin according to the present invention, relatively little insulin is released into the saliva as compared to the blood. This observation suggests that the polypeptide itself contains the information for targeting of secretion.

Preferably, the DNA of interest contains a secretion signal which either directs secretion of the protein primarily into the duct system or directs secretion of the protein primarily into the blood stream. Intravenous-directed secretion signals and duct system-directed secretion signals can be identified by, for example, site-directed mutagenesis of DNA encoding a blood stream-targeted protein (e.g., insulin) or a duct system-targeted protein (e.g., amylase). The mutants can be screened by expression of the mutated DNA in secretory gland cells and subsequently determining the ratio of, for example, salivary to intravenous expression. Alternatively, intravenous-directed secretion signals and duct system-directed secretion signals can also be identified by constructing recombinant, chimeric proteins composed of, for example, a putative intravenous secretion signal inserted into a saliva-directed protein. Intravenous secretion signals would then be identified by their ability to re-direct expression of the saliva-directed protein into the blood stream. Putative intravenous secretion signals and duct system secretion signals can also be identified by comparison of DNA and amino acid sequences of proteins which are preferentially secreted into either the blood stream or the duct system, respectively. Areas of homology or common motifs among the proteins could then be tested as described above.

The DNA of interest may be inserted into a construct so that the therapeutic protein is expressed as a fusion protein (e.g., a fusion protein having β-galactosidase or a portion thereof at the N-terminus and the therapeutic protein at the C-terminal portion). Production of a fusion protein can facilitate identification of transformed cells expressing the protein (e.g., by enzyme-linked immunosorbent assay (ELISA) using an antibody which binds to the fusion protein).

It may also be desirable to produce altered forms of the therapeutic proteins that are, for example, protease resistant or have enhanced activity relative to the wild-type protein. For example, where an enzyme is to be secreted into saliva or pancreatic juices, it may be advantageous to modify the protein so that it is resistant to digestive proteases. Further, where the therapeutic protein is a hormone, it may be desirable to alter the protein's ability to form dimers or multimeric complexes. For example, insulin modified so as to prevent its dimerization has a more rapid onset of action relative to wild-type, dimerized insulin.

The construct containing the DNA of interest can also be designed so as to provide for site-specific integration into the genome of the target secretory gland cell. For example, a construct can be produced such that the DNA of interest and the promoter to which it is operably linked are flanked by the position-specific integration markers of *Saccharomyces cerevisiae* Ty3. The construct for site-specific integration additionally contains DNA encoding a position-specific endonuclease which recognizes the integration markers. Such constructs take advantage of the homology between the Ty3 retrotransposon and various animal retroviruses. The Ty3 retrotransposon facilitates insertion of the DNA of interest into the 5' flanking region of many different tRNA genes, thus providing for more efficient integration of the DNA of interest without adverse effect upon the recombinant cell produced. Methods and compositions for preparation of such site-specific constructs are described in U.S. Pat. No. 5,292,662, incorporated herein by reference with respect to the construction and use of such site-specific insertion vectors.

Transformation

Introduction of the DNA of interest into the secretory gland cell can be accomplished by various methods well known in the art. For example, transformation of secretory gland cells can be accomplished by administering the DNA of interest directly to the mammalian subject (in vivo gene therapy), or to an in vitro culture of a biopsy of secretory glands cells which are subsequently transplanted into the mammalian subject after transformation (ex vivo gene therapy).

The DNA of interest can be delivered to the subject or the in vitro cell culture as, for example, purified DNA, in a viral vector (e.g., adenovirus, mumps virus, retrovirus), a DNA- or RNA-liposome complex, or by utilizing cell-mediated gene transfer. Further, the vector, when present in non-viral form, may be administered as a DNA or RNA sequence-containing chemical formulation coupled to a carrier molecule which facilitates delivery to the host cell. Such carrier molecules can, for example, include an antibody specific to an antigen expressed on the surface of the targeted secretory gland cells, or some other molecule capable of interaction with a receptor associated with secretory gland cells.

The DNA or RNA sequence encoding the molecule used in accordance with the invention may be either locally or systemically administered to the mammalian subject, which may be human or a non-human mammal (e.g., bovine, equine, canine, feline). Where the targeted secretory gland is a salivary gland local administration is preferably by injection into or near a salivary gland or by retrograde perfusion of a salivary gland duct system. More preferably the salivary gland is a parotid gland. Where the targeted secretory gland is the pancreas, local administration is preferably by cannulation of the pancreatic duct by duodenal intubation, using endoscopic retrograde chalangiopancreatography (ECRP).

Systemic administration can be carried out by intramuscular injection of a viral vector containing the DNA of interest. Where the targeted secretory gland is a salivary gland, systemic administration is preferably by oral administration of a viral vector containing a DNA of interest, preferably a adenovirus vector, more preferably a mumps virus vector or other virus vector which substantially specifically infects cells of the salivary gland. Where the targeted secretory gland is the pancreas, systemic administration is preferably achieved by administration of the DNA of interest in a viral vector or DNA-containing formulation (e.g. liposome) which binds the cholecystokinin (CCK) receptor.

As indicated above, the secretory gland cells of a patient may be transformed ex vivo by collecting a biopsy of the secretory gland tissue, culturing secretory gland cells from the biopsy in vitro, and transfecting the cultured secretory gland cells with a DNA of interest in vitro. The resulting transformed secretory gland cells are then implanted into the mammalian subject, preferably into the corresponding secretory gland of the mammalian subject from which the biopsy was taken. Preferably, the secretory gland cells are transformed in vivo by either mechanical means (e.g., direct injection of the DNA of interest into or in the region of the secretory gland or lipofection) or by biological means (e.g., infection of a salivary gland with a non-pathogenic virus, preferably a non-replicative virus, containing the DNA of interest). More preferably, the salivary gland cells are transformed in vivo by infection with a non-replicative virus containing the DNA of interest.

The form of the preparation for transformation of the secretory gland cells will depend upon several factors such as whether transformation is performed ex vivo or in vivo, the secretory gland targeted for gene transfer, the route of administration, and whether a biological or non-biological vector is employed. For example, where the preparation for transformation is administered via the oral route, the preparation may be formulated to provide mucosal resistance (e.g., resistance to proteolytic digestion, denaturation in the mucosal environment, etc.). In addition to the DNA of interest, such oral preparations can include detergents, gelatins, capsules, or other delivery vehicles to protect against degradation.

Generally, transformation is accomplished by either infection of the secretory gland cells with a virus, preferably a replication-deficient virus, containing the DNA of interest, or by a non-viral transformation method, such as direct injection of the DNA into or near the target salivary gland cell, lipofection, "gene gun", or other methods well known in the art. The preferred methodology is dependent upon whether the gene transfer is performed ex vivo or in vivo.

Ex vivo secretory gland gene therapy is accomplished by obtaining a biopsy of tissue from a secretory gland and establishing a primary culture of these secretory gland cells. Methods for obtaining salivary gland tissue biopsy and growing cells from this tissue in vitro are well known in the art. Methods for separation of cells from tissue (see, for example, Amsterdam et al., *J. Cell Biol.* 63:1057–1073, 1974), and methods for culturing cells in vitro are well known in the art.

The secretory gland cells in the in vitro culture are then transformed using various methods known in the art. For example, transformation can be performed by calcium or strontium phosphate treatment, microinjection, electroporation, lipofection, or viral infection. For example, the cells may be injected with a moloney-LTR driven construct or lipofected with an adenovirus-, vaccinia virus-, HIV-, or CMV-promoter construct. The transfected DNA plasmid can contain a selectable marker gene or be co-transfected with a plasmid containing a selectable marker.

Where one or more selectable markers are transferred into the cells along with the DNA of interest, the cell populations containing the DNA of interest can be identified and enriched by selecting for the marker(s). Typically markers provide for resistance to antibiotics such as tetracycline, hygromycin, neomycin, and the like. Other markers can include thymidine kinase and the like.

The ability of the transformed secretory gland cells to express the DNA of interest can be assessed by various methods known in the art. For example, the ability of the cells to secrete the protein into the cell culture media can be examined by performing an ELISA on a sample of cell culture supernatant using an antibody which specifically binds the protein encoded by the DNA of interest. Alternatively, expression of the DNA of interest can be examined by Northern blot to detect mRNA which hybridizes with a DNA probe derived a selected sequence of the DNA of interest. Those cells which express the protein encoded by the DNA of interest can be further isolated and expanded in in vitro culture using methods well known in the art.

After expansion of the transformed secretory gland cells in vitro, the cells are implanted into the mammalian subject, preferably into the secretory gland from which the cells were originally derived, by methods well known in the art. Preferably the cells are implanted in an area of dense vascularization, and in a manner that minimizes evidence of surgery in the subject. The engraftment of the implant of transformed secretory gland cells is monitored by examining the mammalian subject for classic signs of graft rejection, i.e., inflammation and/or exfoliation at the site of implantation, and fever.

In vivo transformation methods normally employ either a biological means of introducing the DNA into the target cells (e.g., a virus containing the DNA of interest) or a mechanical means to introduce the DNA into the target cells (e.g., direct injection of DNA into the cells, liposome fusion, pneumatic injection using a "gene gun"). Generally the biological means used for in vivo transformation of target cells is a virus, particularly a virus which is capable of infecting the target cell, and integrating at least the DNA of interest into the target cell's genome, but is not capable of replicating. Such viruses are referred to as replication-deficient viruses or replication-deficient viral vectors. Alternatively, the virus containing the DNA of interest is attenuated, i.e. does not cause significant pathology or morbidity in the infected host (i.e., the virus is nonpathogenic or causes only minor disease symptoms).

Numerous viral vectors useful in in vivo transformation and gene therapy are known in the art, or can be readily constructed given the skill and knowledge in the art. Exemplary viruses include non-replicative mutants/variants of adenovirus, mumps virus, retrovirus, adeno-associated virus, herpes simplex virus (HSV), cytomegalovirus (CMV), vaccinia virus, and poliovirus. Preferably, the replication-deficient virus is capable of infecting slowly replicating and/or terminally differentiated cells, since secretory glands are primarily composed of these cell types. Thus, adenovirus is a preferred viral vector since this virus efficiently infects slowly replicating and/or terminally differentiated cells. More preferably, the viral vector is specific or substantially specific for cells of the targeted secretory salivary gland. For example, the mumps virus is particularly preferred where the targeted secretory gland is a salivary gland.

In vivo gene transfer using a biological means can be accomplished by administering the virus containing the DNA to the mammalian subject either by an intraductal route, an oral route, or by injection depending upon the secretory gland targeted for gene transfer. The amount of DNA and/or the number of infectious viral particles effective to infect the targeted secretory gland, transform a sufficient number of secretory gland cells, and provide for expression of therapeutic levels of the protein can be readily determined based upon such factors as the efficiency of the transformation in vitro, the levels of protein expression achieved in vitro, and the susceptibility of the targeted secretory gland cells to transformation. For example, where the targeted secretory gland is a salivary gland and where a virus containing the DNA of interest is administered orally, the virus will be administered at a concentration effective to infect salivary gland cells of the mammalian subject and provide for therapeutic levels of the protein in either the blood or the saliva.

Various mechanical means can be used to introduce a DNA of interest directly into a secretory gland for expression in a secretory gland cell of a mammalian subject. For example, the DNA of interest may be introduced into a salivary gland by percutaneous injection or by retrograde injection via the ducts leading from the oral mucosa to the salivary gland. Preferably, the DNA is injected percutaneously into the parotid gland of the mammalian subject. Where the secretory gland is the pancreas, direct administration of the DNA of interest into the pancreas can be accomplished by cannulation of the pancreatic duct by, for example duodenal intubation. Alternatively, administration of the virus containing the DNA of interest may be accomplished by intramuscular injection.

The DNA of interest may be naked (i.e., not encapsulated), provided as a formulation of DNA and cationic compounds (e.g., dextran sulfate), or may be contained within liposomes. Alternatively, the DNA of interest can be pneumatically delivered using a "gene gun" and associated techniques which are well known in the art (Fynan et al. *Proc. Natl. Acad. Sci. USA* 90:11478–11482, 1993). Where the targeted secretory gland is a salivary gland, the DNA of interest is preferably introduced by direct percutaneous injection of naked DNA into the salivary gland, preferably into the parotid gland.

The amount of DNA administered will vary greatly according to a number of factors including the susceptibility of the target cells to transformation, the size and weight of the subject, the levels of protein expression desired, and the condition to be treated. For example, the amount of DNA injected into a secretory gland of a human is generally from about 1 μg to 200 mg, preferably from about 100 μg to 100 mg, more preferably from about 500 μg to 50 mg, most preferably about 10 mg. The amount of DNA injected into the pancreas of a human is, for example, generally from about 1 μg to 750 mg, preferably from about 500 μg to 500 mg, more preferably from about 10 mg to 200 mg, most preferably about 100 mg. Generally, the amounts of DNA for human gene therapy can be extrapolated from the amounts of DNA effective for gene therapy in an animal model. For example, the amount of DNA for gene therapy in a human is roughly 100 times the amount of DNA effective in gene therapy in a rat. The amount of DNA necessary to accomplish secretory gland cell transformation will decrease with an increase in the efficiency of the transformation method used.

Intravenous and Gastrointestinal Protein Therapy by Transformation of Salivary Gland Cells Secretory glands transformed according to the invention facilitate high level expression of a DNA of interest, particularly where the DNA of interest is operably linked to a strong eukaryotic promoter (e.g., CMV, MMTV, or pancreatic or salivary amylase promoters). The expressed protein is then secreted at high levels into the blood stream or into the gastrointestinal tract via saliva or pancreatic juices. The protein so expressed and secreted is thus useful in treating a mammalian subject having a variety of conditions. For example, secretion of an appropriate protein into the saliva is useful in preventing or controlling various upper gastrointestinal tract diseases, e.g., in treating chronic infections of the oral cavity, (e.g., bacterial or fungal infections); in treating degenerative disorders of the salivary glands, in treating salivary glands damaged by irradiation; or as a replacement or supplemental protein therapy. Secretion of an appropriate protein into the pancreatic juices is useful in preventing or controlling various lower gastrointestinal diseases, e.g. in treating chronic infections of the stomach and/or intestinal tract; in treating degenerative pancreatic disorders; or as a replacement or supplemental protein therapy (e.g., diabetes, intrinsic factor deficiency, digestive enzyme deficiencies).

In a preferred embodiment, the proteins are secreted into the blood stream at levels sufficient for intravenous protein therapy. For example, the normal amount of a specific protein released into the blood from the pancreas can be substantial, e.g. as much as 25% of the amount of duct-directed protein secretion. Blood stream levels of the therapeutic protein may be enhanced by integration of multiple copies of the DNA of interest into the genome of the target cells, and/or by operably linking a strong promoter (e.g., a promoter from CMV) and/or enhancer elements to the DNA of interest in the construct. Blood stream levels may also be enhanced by implanting a greater number of transformed cells (ex vivo gene therapy) or transformation of a greater number of target cells in the subject (in vivo gene therapy). As discussed above, secretion of the therapeutic protein may also be enhanced by incorporating leader sequences, amino acid sequence motifs, or other elements which mediate intravenous-directed secretion into the sequence of the therapeutic protein.

Overall secretion from secretory glands is augmented by hormonal stimulation. For example, where the protein is primarily secreted into the duct system and is secreted at lower levels into the blood stream, hormonal stimulation enhances both ductal and intravenous secretion. Thus, therapeutically effective levels of the protein in the gastrointestinal tract and the blood stream may be achieved or enhanced by administration of an appropriate, secretory gland specific hormone. For example, secretory gland secretion can be enhanced by administration of a cholinergic agonist such as acetyl-β-methyl choline.

The actual number of transformed secretory gland cells required to achieve therapeutic levels of the protein of interest will vary according to several factors including the protein to be expressed, the level of expression of the protein by the transformed cells, the rate of protein secretion, the partitioning of the therapeutic protein between the gastrointestinal tract and the blood stream, and the condition to be treated. For example, the desired intravenous level of therapeutic protein can be readily calculated by determining the level of the protein present in a normal subject (for treatment of a protein deficiency), or by determining the level of protein required to effect the desired therapeutic result. The level of expression of the protein from transformed cells and the rate of protein secretion can be readily determined in vitro. Given the in vitro levels of protein expression and secretion, and the estimated intravenous level of therapeutic protein desired, the number of cells which should be transformed to effect the desired levels can be readily calculated, and the gene therapy protocol carried out accordingly.

Figure 3A:
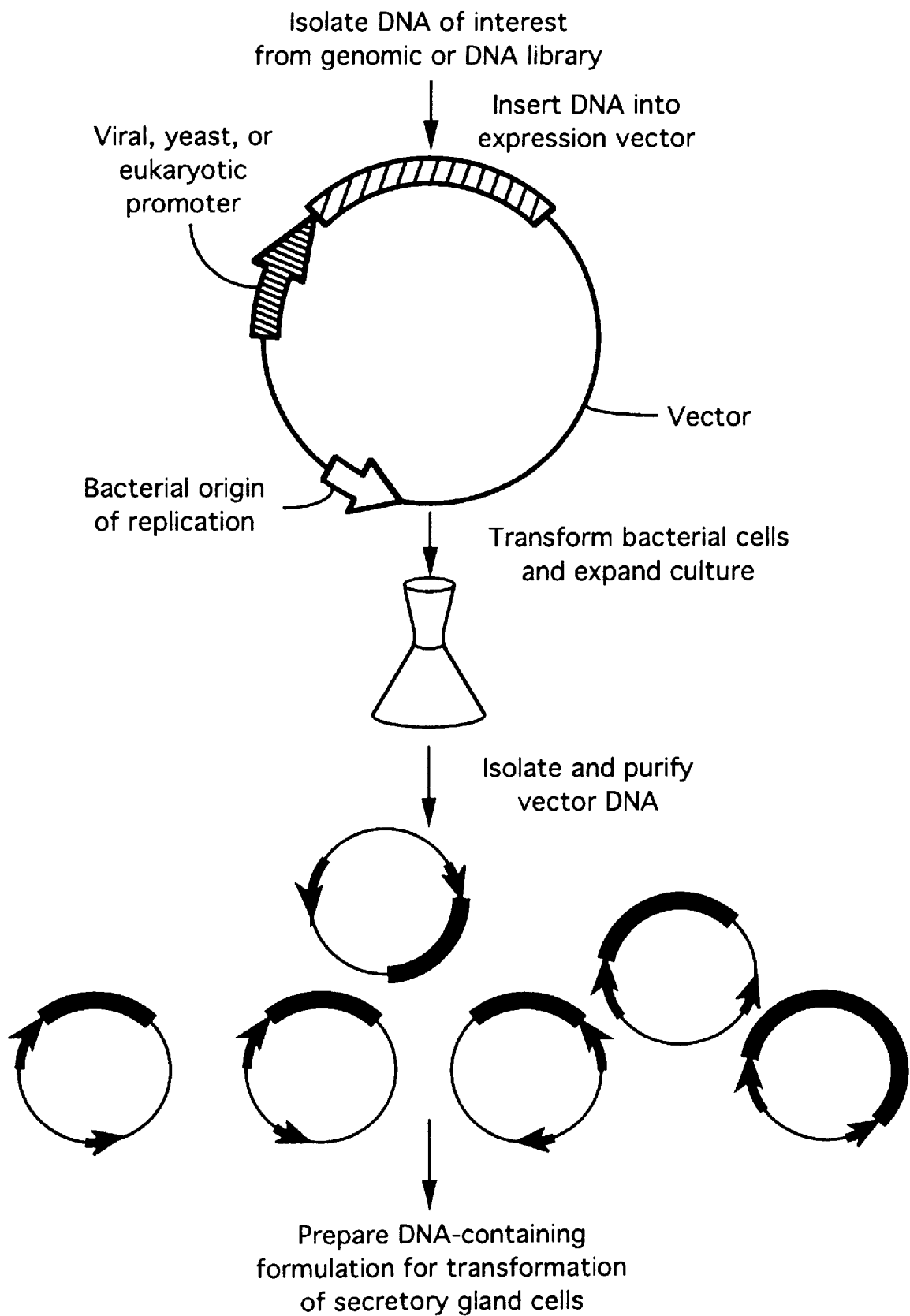
FIGS. 3A and 3B are a schematic flow diagrams of production of recombinant secretory gland cells and their use in a therapeutic method of the invention.
Figure 3B:
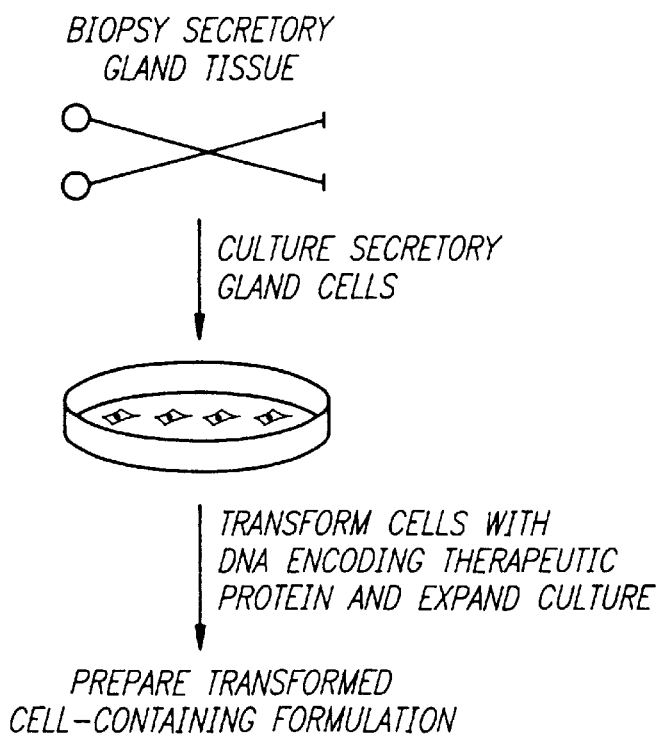
Figure 3B:
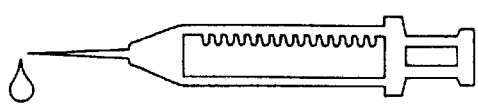
Figure 3B:
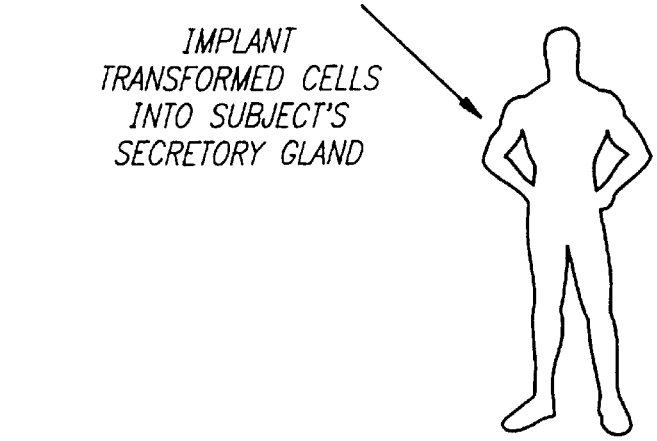

A general schematic diagram showing the production of vectors and transformed secretory gland cells according to the invention is provided in FIGS. 3A and 3B.

Assessment of Protein Therapy

Following either ex vivo or in vivo transfer of a DNA of interest into a secretory gland, the effects of expression of the protein encoded by the DNA of interest can be monitored in a variety of ways. Generally, the presence of the protein in either a sample of blood, or a sample of saliva, pancreatic juices, urine, or mucosal secretions from the subject can be assayed for the presence of the therapeutic protein. Appropriate assays for detecting a protein of interest in either saliva or blood samples are well known in the art. For example, where secretory gland gene therapy has been performed to accomplish intravenous protein therapy, a sample of blood can be tested for the presence of the protein using an antibody which specifically binds the therapeutic protein in an ELISA assay. This assay can be performed either qualitatively or quantitatively. The ELISA assay, as well as other immunological assays for detecting a protein in a sample, are described in *Antibodies: A Laboratory Manual* (1988, Harlow and Lane, ed.s Cold Spring Harbor Laboratory, Cold Spring Harbor, N.Y.).

Alternatively, or in addition, the efficacy of the protein therapy can be assessed by testing a sample of blood, or saliva, or pancreatic juices or mucosal secretion for an activity associated with the therapeutic protein (e.g., an enzymatic activity). For example, where the therapeutic protein has antimicrobial activity, the efficacy of therapy can be tested by examining the ability of the test sample to inhibit bacterial growth. Furthermore, the efficacy of secretory gland gene therapy can be assessed by monitoring the condition of the mammalian subject for improvement. For example, where the therapeutic protein is erythropoietin, the subject's blood is examined for iron content or other parameters associated with anemia. Where the therapeutic protein is insulin, the efficacy of the therapy can be assessed by examining blood glucose levels of the mammalian subject or by measuring insulin (e.g., by using the human insulin radioimmunoassay kit, Linco Research Inc., St. Louis, Mo.).

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

In vivo Gene Transfer to Salivary Glands by Injection of Naked DNA Encoding Insulin Four adult rats weighing approximately 300 g each were anesthetized with an intraperitoneal injection of sodium pentobarbital. An incision was made parallel to the line of the mandible and both parotid glands exposed by dissection. Two rats received a total of 100 µl of 0.5 µg/µl pBAT14.hIns plasmid which contains cDNA encoding human insulin (FIG. 1), while the remaining two rats received 100 µl 0.9% saline (sham animals). The test and control samples were administered by multi-site subcapsular injection to each parotid gland of each animal. No significant leakage of material or bleeding occurred. The wound was closed after administration. After 3 hours, the animals were awake, drinking water, and appearing normal.

Approximately 24 hours after cDNA injection, the animals were again anesthetized and a tracheostomy performed. A control blood sample was drawn from the femoral vein of each animal. The cholinergic agonist acetyl-β-methyl choline (McH) was injected into each subcutaneously at 0.8 mg/kg body weight into each animal. The salivary glands appeared normal and showed no signs of inflammation. Twenty minutes after McH injection, saliva and blood samples were collected from each animal. The blood samples were collected from the inferior vena cava and by heart puncture. Serum was separated from the blood of all samples after clotting, and kept at −20° C. prior to assay. In addition, blood was collected from 10 normal rats, and serum prepared to determine the blood level of insulin in untreated rats.

The results of this experiment are shown in Table 3. The level of insulin in the blood of transfected animals and in blood of untransfected animals was essentially the same. Administration of McH induced an increase in serum insulin levels in both the control and transfected animals. The concentration of insulin was higher after McH stimulation in the two transfected animals than in the McH-stimulated control animals.

TABLE 3

| Treatment | Insulin (µU/ml) |
|---|---|
| Normal (untreated) | 2.6 |
| cDNA 1 | |
| −McH | 1.4 |
| +McH | 10.0 |
| cDNA 2 | |
| −McH | 2.5 |
| +McH | 11.6 |
| Control 1 | |
| −McH | 2.0 |
| +McH | 5.6 |
| Control 2 | |
| −McH | 2.0 |
| +McH | 9.2 |

Example 2

In vivo Gene Transfer to Salivary Glands by Injection of an Increased Dosage Naked DNA Encoding Insulin In a second experiment, four adult rats weighing approximately 300 g each were anesthetized with an intraperitoneal injection of sodium pentobarbital. Two rats received a total of 100 µl of 1–1.2 µg/µl pBAT14.hIns plasmid containing cDNA encoding human insulin, while the remaining two rats received 100 µl 0.9% saline (control animals). The test and control samples were administered by multi-site subcapsular injection to each parotid gland of each animal as described above in Example 1, and the wound closed after administration.

Approximately 24 hours after injection, the animals were again anesthetized, blood samples drawn from each animal, and the cholinergic agonist McH administered at 0.8 mg/kg body weight by subcutaneous injection. Twenty minutes after McH injection, blood samples were drawn from the inferior vena cava and by heart puncture of each animal. Serum was separated from the blood of all samples after clotting, and kept at −20° C. prior to assay for insulin. The parotid glands of all animals looked normal and showed no signs of inflammation.

As shown in Table 4, the levels of insulin in the blood of the transfected animals was substantially higher than in the previous experiment, suggesting that the increased dosage of cDNA resulted in increased insulin production. Insulin levels in the transfected animals were elevated by McH stimulation. Moreover, the animals transfected with 100 μg–120 μg cDNA had about 50% greater insulin levels after McH stimulation than the animals transfected with 50 μg cDNA described above.

TABLE 4

| Treatment | Insulin (μU/ml) |
| --- | --- |
| cDNA 3 | |
| −McH | 6.4 |
| +McH | 15.2 |
| cDNA 4 | |
| −McH | 7.2 |
| +McH | 15.2 |

Example 3

Effects of Isoprenaline Stimulation on Expression of Insulin Following in vivo Transformation of Salivary Glands Two transfected rats and two control rats were treated using the same protocol, vector, and dose as in Example 2. Approximately 24 hours after injection, the animals were again anesthetized, blood samples drawn from each animal, and the adrenergic agonist isoprenaline (IsO) was administered at 0.1 μg/kg body weight by subcutaneous injection. Twenty.minutes after Iso injection, blood samples were drawn from the inferior vena cava and by heart puncture of each animal. Serum was separated from the blood of all samples after clotting, and kept at −20° C. prior to assay for insulin.

As shown in Table 5, the blood insulin levels in the transfected animals was substantially elevated relative to control values. Injection of Iso had no effect upon blood insulin levels.

TABLE 5

| Treatment | Insulin (μU/ml) |
| --- | --- |
| cDNA 5 | |
| −IsO | 8.5 |
| +IsO | 8.0 |
| cDNA 6 | |
| −IsO | 6.4 |
| +IsO | 8.0 |

Example 4

Effects of Streptozotocin on Insulin Levels in Rats Following in vivo Transfer of cDNA Encoding Insulin to Salivary Glands Streptozotocin, which induces diabetes mellitus in rats, was administered to three adults rats weighing approximately 220–230 g at 70 mg/kg body weight by intraperitoneal injection. The animals were anesthetized by intraperitoneal injection of sodium pentobarbital. Two of the animals were injected with a 50 μl volume of 2 μg/μl pBAT14.hIns plasmid which contains cDNA encoding human insulin. The remaining rat received 100 μl 0.9% saline (control animal). The test and control samples were administered by multi-site subcapsular injection to each parotid gland of each animal as described in Example 1.

Approximately 48 hours after cDNA or saline injection, the animals were again anesthetized and a tracheostomy performed. A control blood sample was drawn from the femoral vein of each animal. McH was administered at 0.8 mg/kg body weight by subcutaneous injection. Twenty minutes after McH injection, saliva and blood samples were collected from each animal. The blood samples were collected from the inferior ven cava and by heart puncture. Serum was separated from the blood of all samples after clotting, and kept at −20° C. prior to assay. In addition, the salivary glands and a portion of the pancreas were removed and homogenized in 50 mM phosphate buffer (pH 8.0) 1:10 w/v. The homogenates were spun at 50,000×g for 1 h and the supernatant stored at −20° C. A small portion of parotid and salivary glands were fixed in 10% buffered formalin and saved for histologic examination. The parotid glands showed no observable signs of inflammation as a results of cDNA injection.

As shown in Table 6, streptozotocin administration decreased the blood levels of insulin in the transfected animals. Stimulation with McH was effective in increasing serum insulin levels in one of the two transfected animals, but not in the control animal.

TABLE 6

| Treatment | Insulin (μU/ml) | Glucose (mg/dl) |
| --- | --- | --- |
| cDNA | | |
| −McH | 0.5 | 268 |
| +McH | 8.8 | 385 |
| cDNA | | |
| −McH | 1.6 | 321 |
| +McH | 1.0 | 413 |
| Control | | |
| −McH | 5.2 | 230 |
| +McH | 4.8 | 335 |

Example 5

Summary of Results of in vivo Gene Transfer to Salivary Glands by Percutaneous Injection of Naked DNA Encoding Insulin Nine adult rats were anesthetized with an intraperitoneal injection of sodium pentobarbital. Six rats were injected percutaneously with DNA encoding insulin. Two rats received a 100 μl volume of 0.5 μg/μl pBAT14.hIns plasmid which contains cDNA encoding human insulin (low dose animals), while the four other transfected rats received a 100 μl volume of 1.0 μg/μl pBAT14.hIns (high dose animals). The remaining three rats received 100 μl 0.9% saline (sham animal).

Approximately 24 hours after injection, the animals were again anesthetized. Control blood samples were drawn from the femoral vein of each animal. Two of the control animals, two of the low dose animals, and two of the high dose animals received a subcutaneous injection of 0.8 mg/kg body weight McH. Two of the high dose transfected animals received a subcutaneous injection of the adrenergic agonist IsO at 0.1 μg/kg body weight. Twenty minutes after McH or Iso injection, saliva and blood samples were collected from each animal. The blood samples were collected from the inferior ven cava and by heart puncture. Serum was separated from the blood of all samples after clotting, and kept at −20° C. prior to assay.

The results of this experiment are shown in Table 7. The serum insulin levels were highest in the high dose transfected animal group. The serum insulin levels of the low dose transfected group and the control group were similar. After stimulation with McH, serum insulin levels were again markedly higher in the high dose transfected group than in either the low dose transfected or the control groups. Serum insulin levels after McH stimulation were higher in the low dose transfected group than in the control group. Iso injection of high dose transfected rats had no significant effect upon serum insulin levels as compared to serum insulin levels in the absence of agonist. These data show that high dose cDNA increase both unstimulated (-McH) and McH-stimulated insulin responses.

TABLE 7

Average values for the effect percutaneous administration of human insulin cDNA to parotid gland on serum insulin

| Treatment | Insulin (μU/ml) |
|---|---|
| Control | 2.5 (12) |
| Low dose cDNA (0.5 μ/μl) | 2.0 (2) |
| High dose cDNA (1.0 μg/μl) | 7.4 (6) |
| With cholinergic-stimulation (McH) | |
| Control | 7.6 (2) |
| Low dose cDNA (0.5 μg/μl) | 13.0 (2) |
| High dose cDNA (1.0 μg/μl) | 15.2 (2) |

( ) = # of animals

Example 6

Ex vivo Gene Transfer of DNA Encoding Erythropoietin into a Human Salivary Gland A biopsy of a human parotid gland is obtained by surgical incision and extraction of a small (1 cm$^2$) tissue sample. The tissue sample is passed through a sterile 1 mm$^2$ mesh screen to provide a single cell suspension of salivary gland cells. The cells are transferred to a tissue culture flask and incubated in complete tissue culture medium in a tissue culture incubator at 37° C., 5% $CO_2$. When the flask reaches approximately 70% to 90% confluency, the cells are removed from the flask by incubation in sterile phosphate-buffered saline (PBS) containing EDTA. The cells are then split into two flasks and incubation is continued. After these cells reach confluency in the flasks, the culture medium is replaced with medium containing liposomes containing DNA encoding erythropoietin. The erythropoietin DNA is operably linked to the salivary amylase promoter and is additionally linked to a gene encoding neomycin resistance. The cells are incubated for 24 hrs in the presence of the liposome-containing medium. The medium is then removed and replaced with fresh medium containing neomycin. After an additional two to three days incubation, the cells are again split into two flasks and grown to confluency.

To determine whether the transformed cells are producing and secreting erythropoietin, a sample of the cell culture medium is examined by Western blot. Briefly, the cell supernatant sample is collected and concentrated by ultrafiltration using a filter which allows filtration of proteins of only an appropriate molecular weight range. Protein concentration is determined using Lowry's method (Lowry et al., *J. Biol. Chem.* 193:265–275, 1951). The samples are then subjected to polyacrylamide gel electrophoresis. The size of the protein(s) is estimated using prestained protein molecular weight standards. the electrophoresed proteins are transferred to nitrocellulose membranes and the transferred proteins detected by Western blotting (Towbin et al., *Proc. Natl. Acad. Sci. USA* 76:4350–4354, 1979) using a mixture of mouse antisera against the protein encoded by the DNA of interest. The immunoblots are developed by incubating the antibodies with goat anti-mouse IgG conjugated to alkaline phosphatase. The conjugate is made visible by reaction of the immunoblot with the chromogenic substrate 5-bromo-4-chloro-3-indolyl-phosphate/p-nitro blue tetrazolium chloride. Expression and secretion of erythropoietin by the transformed cells is correlated with the presence of a protein band of appropriate molecular weight on the immunoblot.

The transformed cells are then removed from the flasks and implanted into the parotid gland of the patient. The establishment and acceptance of the implant is monitored at least daily. The expression of erythropoietin by the implant and the secretion of erythropoietin into the blood stream of the patient are determined by ELISA. Briefly, a sample of blood is collected and the sample subjected to centrifugation. The serum is then collected and applied to a microtiter plate having bound to its surface an anti-erythropoietin antibody. The wells of the plate are then washed with buffer, and a second anti-erythropoietin antibody is applied to the wells. Following incubation, the wells are again washed to rid of excess second antibody, and an antibody which specifically binds the second, fluorescently labeled anti-erythropoietin antibody is applied to the wells. After a final incubation and washing step to rid of unbound material, the label is then detected with an ELISA reader. Detection of a fluorescent signal is indicative of the presence of erythropoietin in the blood sample and thus the expression and secretion of erythropoietin by the implanted cells.

Example 7

In vivo Gene Transfer of DNA Encoding Clotting Factor VIII by Oral Infection with a Replication-deficient Adenovirus A DNA fragment containing the DNA sequence encoding clotting factor VIII (Gitschier et al. *Nature*, 312:326–330, 1984; Wood et al. *Nature*, 312:330–337, 1984) is operably linked to the moloney-LTR promoter. This promoter-clotting factor VIII cassette is inserted into a replication-deficient recombinant adenovirus vector. The adenovirus vector has been constructed so that the 5' end of the E1 promoter and a portion of the E3 regions are deleted. The promoter-clotting factor VIII DNA cassette is inserted at the site of the E1 deletion. Adenovirus vectors are prepared, purified, and titered as previously described (Rosenfeld et al. *Science* 252:431–434, 1991; Rosenfeld et al., *Cell* 68:143–155, 1992).

Approximately 5×10$^9$ pfu (plaque-forming units) of the recombinant virus containing clotting factor VIII DNA are orally administered. Expression of the clotting factor VIII DNA and intravenous secretion of clotting factor VIII are assessed as described above.

Example 8

In vivo Gene Transfer of DNA Encoding Human Growth Hormone by Retrograde Injection of DNA A DNA fragment encoding human growth hormone (hGH) is operably linked to the LTR of Rous sarcoma virus, which serves as a promoter, and the SV40 type T antigen, which serves as a nuclear localization signal. This promoter-localization signal-hGH DNA cassette is then inserted into the bacterial plasmid pBR322. *Escherichia coli* is then transformed with the plasmid using conventional transformation procedures. *E. coli* containing the plasmid are selected by virtue of the tetracycline or ampicillin resistance encoded by pBR322, and the transformed bacterial cells propagated in culture. Plasmid DNA is then isolated from the transformed bacterial cell culture and the DNA purified by cesium gradient.

Approximately 10 mg to 20 mg of the purified plasmid DNA containing hGH DNA is injected into the salivary gland of a human patient by retrograde injection via a salivary gland duct. Expression and intravenous secretion of the protein is assessed using the method described above.

Example 9

Figure 4:
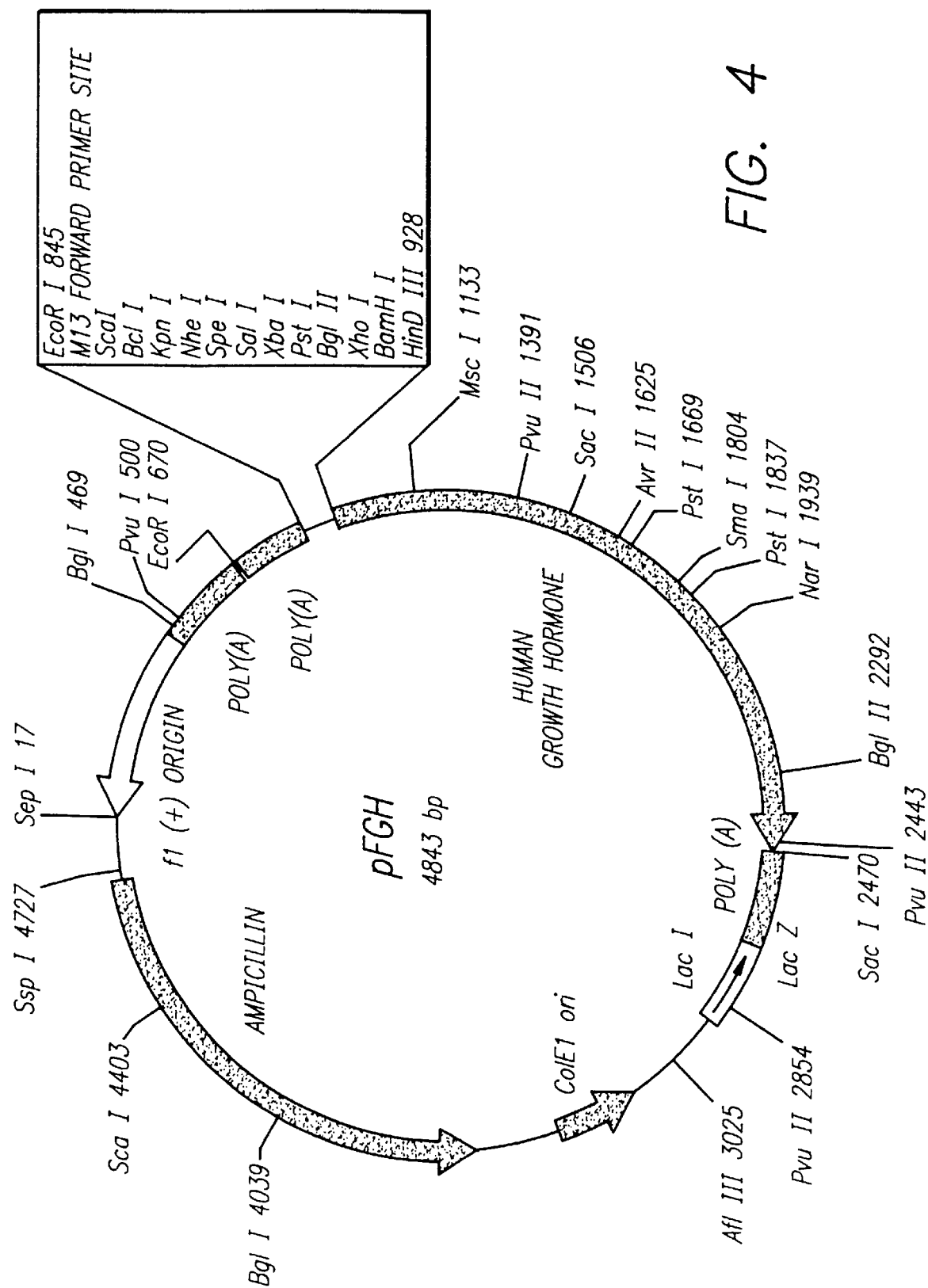
FIG. 4 is a map of the PFGH construct, which contains the human growth hormone genomic sequence.
Figure 5:
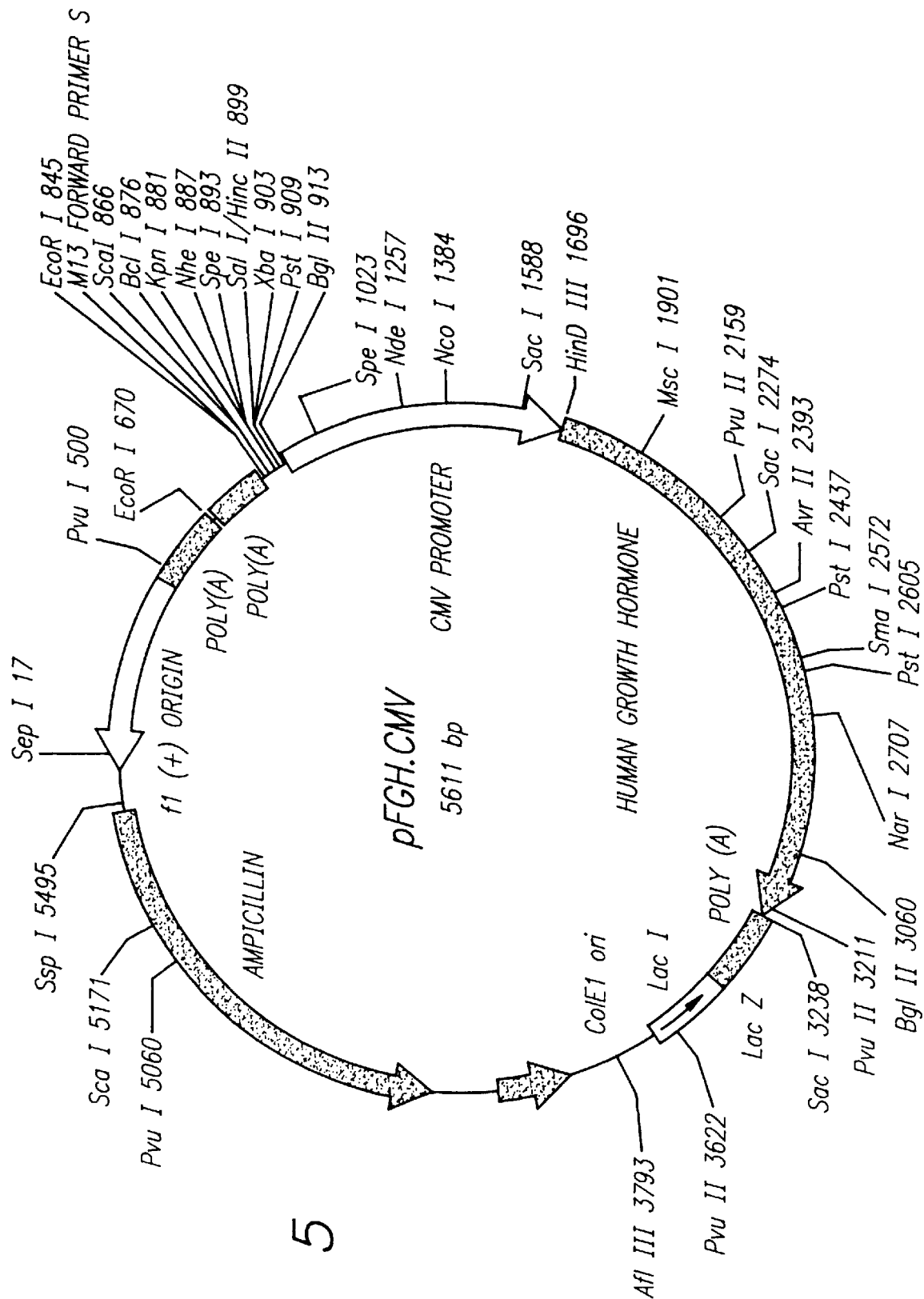
FIG. 5 is a map of the pFGH.CMV construct, which contains the human growth hormone genomic sequence operably linked to the CMV promoter.
Figure 6:
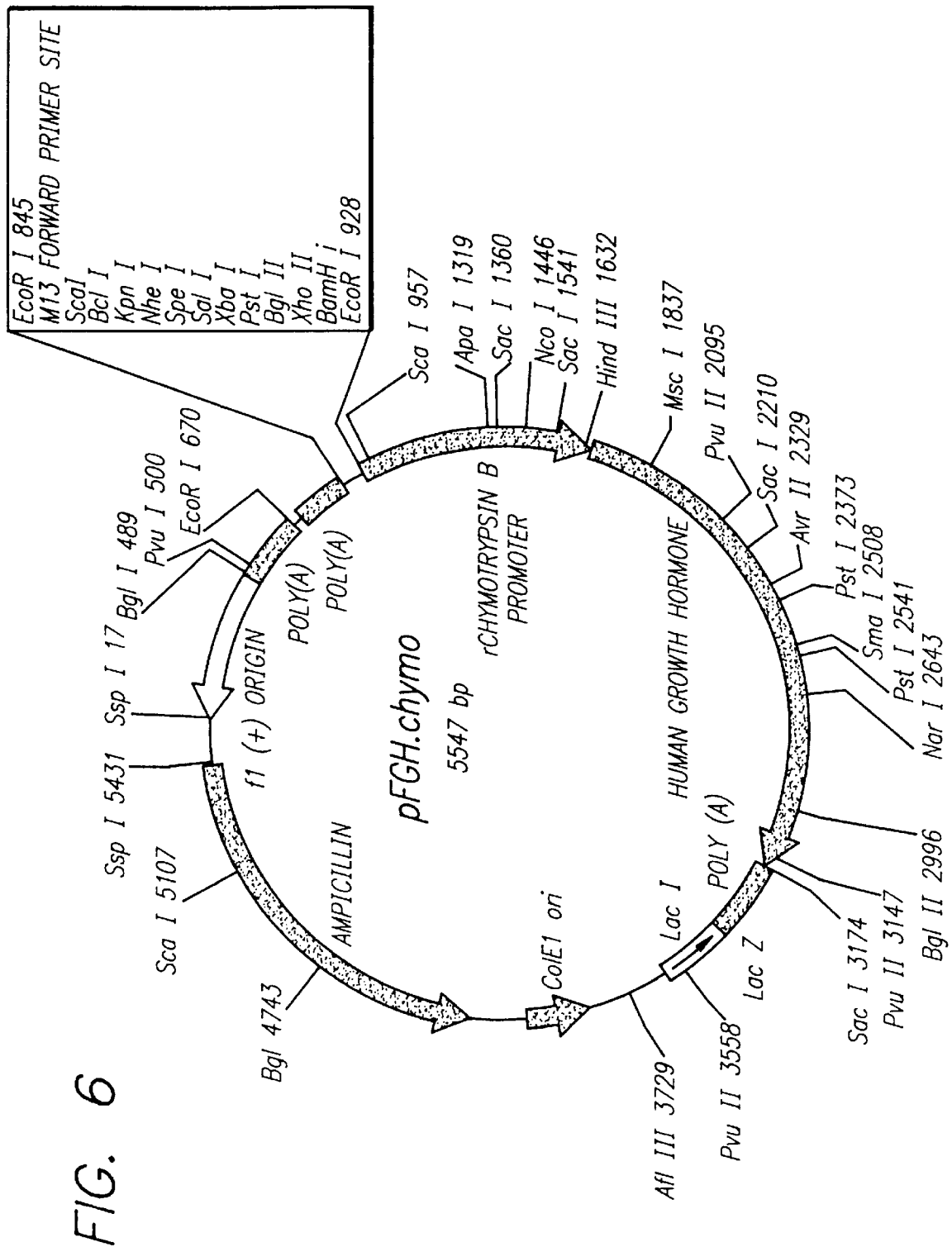
FIG. 6 is a map of the pFGH.chymo construct, which contains the human growth hormone genomic sequence operably linked to the chymotrypsin B promoter.

In vivo Gene Transfer of DNA Encoding Human Growth Hormone by Retrograde Injection of DNA into the Pancreas Four constructs for expression of human growth hormone (hGH) were prepared using techniques well known in the art (see, for example, Sambrook et al. ibid). The first construct, pFGH, contains the genomic hGH DNA sequence inserted in the commercially available vector PBLUESCRIPT SK+™ (Stratagene, LaJolla, Calif.) (FIG. 4). Because the hGH coding sequence is not linked to a promoter, this vector provides for no or only low-level hGH expression. Thus, the PFGH construct serves as a negative control for hGH expression in the pancreas. The second construct, pFGH.CMV, was constructed by operably inserting the promoter from the immediate early gene of human CMV upstream of the genomic hGH sequence of the pFGH vector (FIG. 5). The third construct, pFGH.chymo, was constructed by operably inserting the rat chymotrypsin B gene promoter upstream of the genomic hGH sequence of the pFGH vector (FIG. 6). The fourth construct, pFGH.RSV, was constructed by operably inserting the promoter from the long terminal repeat (LTR) of RSV upstream of the genomic hGH sequence of the PFCH vector.

Each of the four vectors was used to transfect the pancreas of approximately 300 g adult rats (pFGH+lipofectin, 4 rats; pFGH.chymo+lipofectin, 4 rats; pFGH.RSV+lipofectin, 4 rats; pFGH.CMV+lipofectin, 10 rats; pFGH.CMV without lipofectin, 7 rats; negative control (no DNA, no lipofectin), 3 rats). Pancreatic transfection was accomplished by first anesthetizing the rats and erforming a laparotomy to expose the duodenum. The ancreas and the associated common bile duct were identified, and the common bile duct was cannulated either extraduodenally or through the papilla of Vater. The hepatic duct was occluded, and 100 μl of phosphate-buffered saline (PBS) containing one of the four vectors, or 100 μl of PBS alone as a negative control, were slowly injected or infused into the pancreatic duct in a retrograde direction. The vector-containing solutions were composed of 8 μg DNA per 100 μl in PBS, either with or without 6% lipofectin, a cationic lipid used to increase transfection efficiency. The solution was left in place for 5 min before secretory flow was allowed to resume and hepatic duct blockage removed. The catheter was left in place and inserted into the duodenum through a small hole to ensure adequate biliary and pancreatic flow post-operatively. The abdomen was then closed with sutures. The animals recovered fully and rapidly from the surgery without obvious side effects. This transfection method provides direct access of the vector to over 90% of the pancreatic gland cells.

At 48 hr after surgery, a blood sample was obtained to measure serum hGH levels, and the rats were sacrificed. At autopsy, the pancreas of both control and test rats appeared normal, and exhibited no gross or microscopic pathology.

The pancreas was dissected free from the mesenteric surface and was homogenized in cold 0.2M (pH 8.0) sodium phosphate buffer (1:10 w/v) containing protease inhibitors aprotinin, leupeptin, pepstatin, and PEFABLOC SC™. Homogenization was completed by shearing after 10 passes with a motorized pestle at approximately 4000 rpm in a glass homogenizer. The homogenate was then centrifuged at 1000 g for 15 min. The supernatant was collected and stored at −80° C. until analysis. The levels of hGH in the serum and pancreatic protein samples were measured using the hGH radioimmune assay (Nichols Institute). Each assay was performed in duplicate and compared to a set of control samples.

Figure 7:
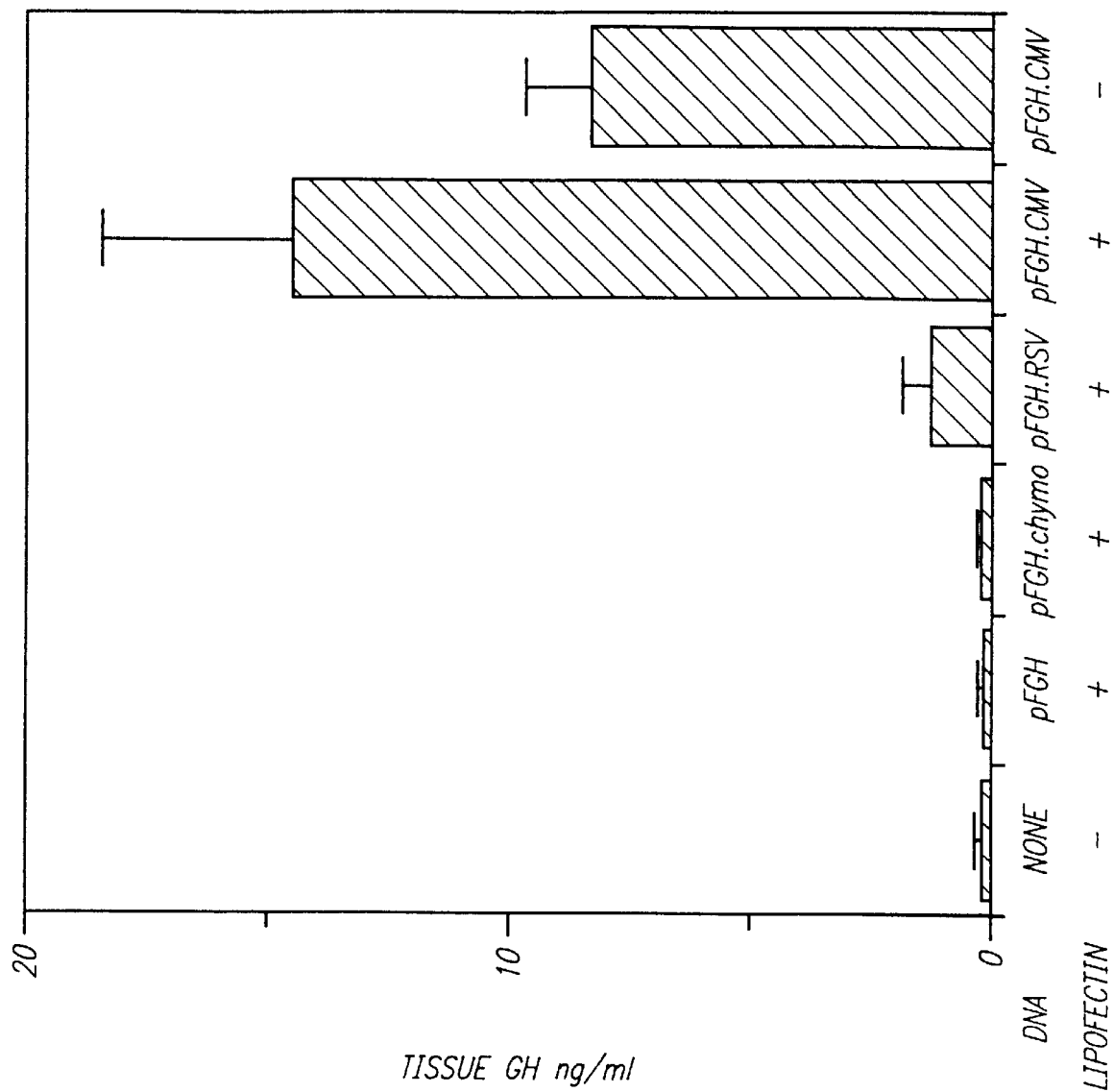
FIG. 7 is a graph showing the levels of tissue expression of human growth hormone expression in the pancreas of rats after retrograde injection with either a control containing no DNA or a test sample containing a human growth hormone construct.
Figure 8:
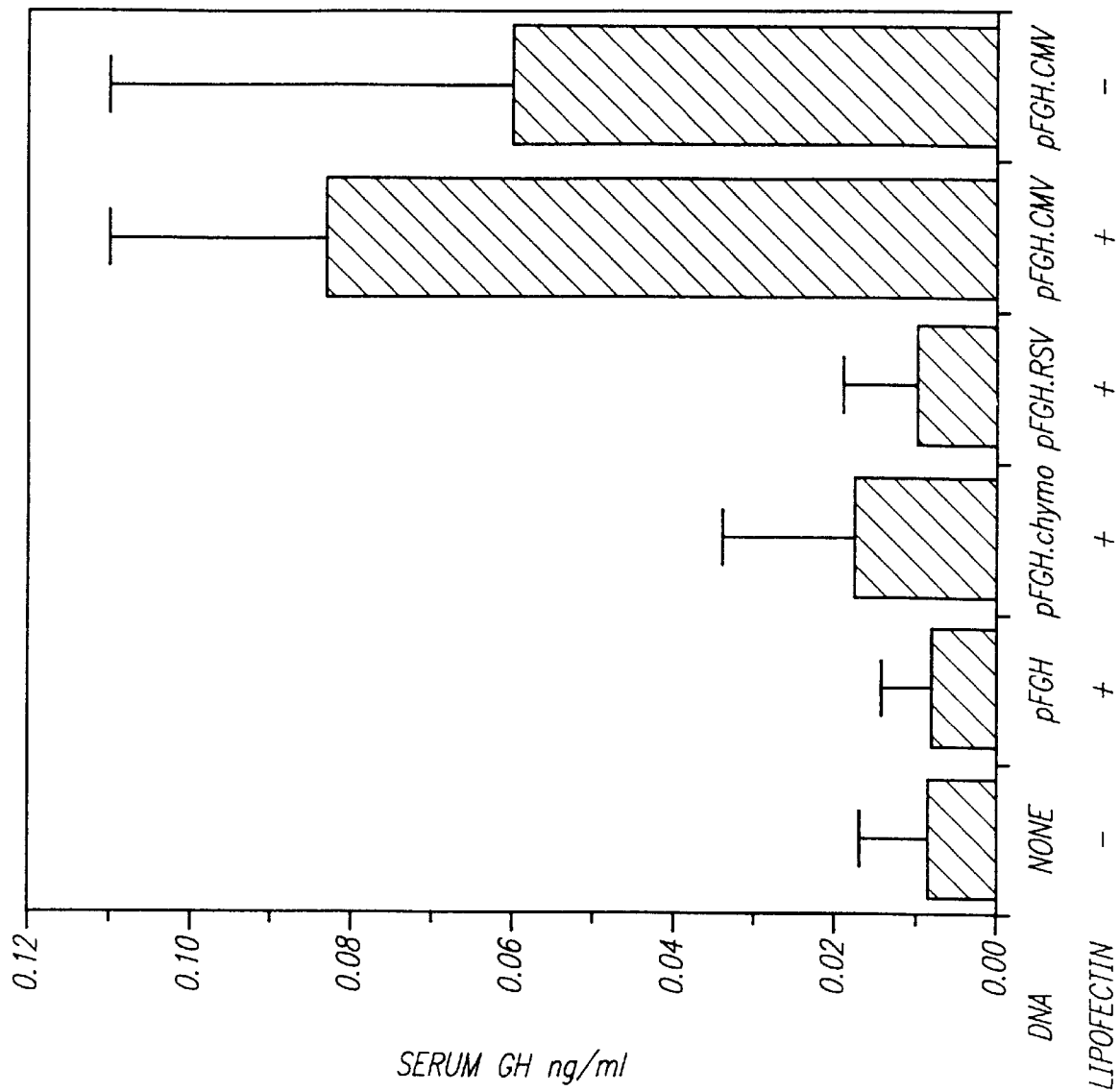
FIG. 8 is a graph showing the serum levels of human growth hormone in rats after retrograde pancreatic injection with either a control containing no DNA or a test sample containing a human growth hormone construct.
Figure 9:
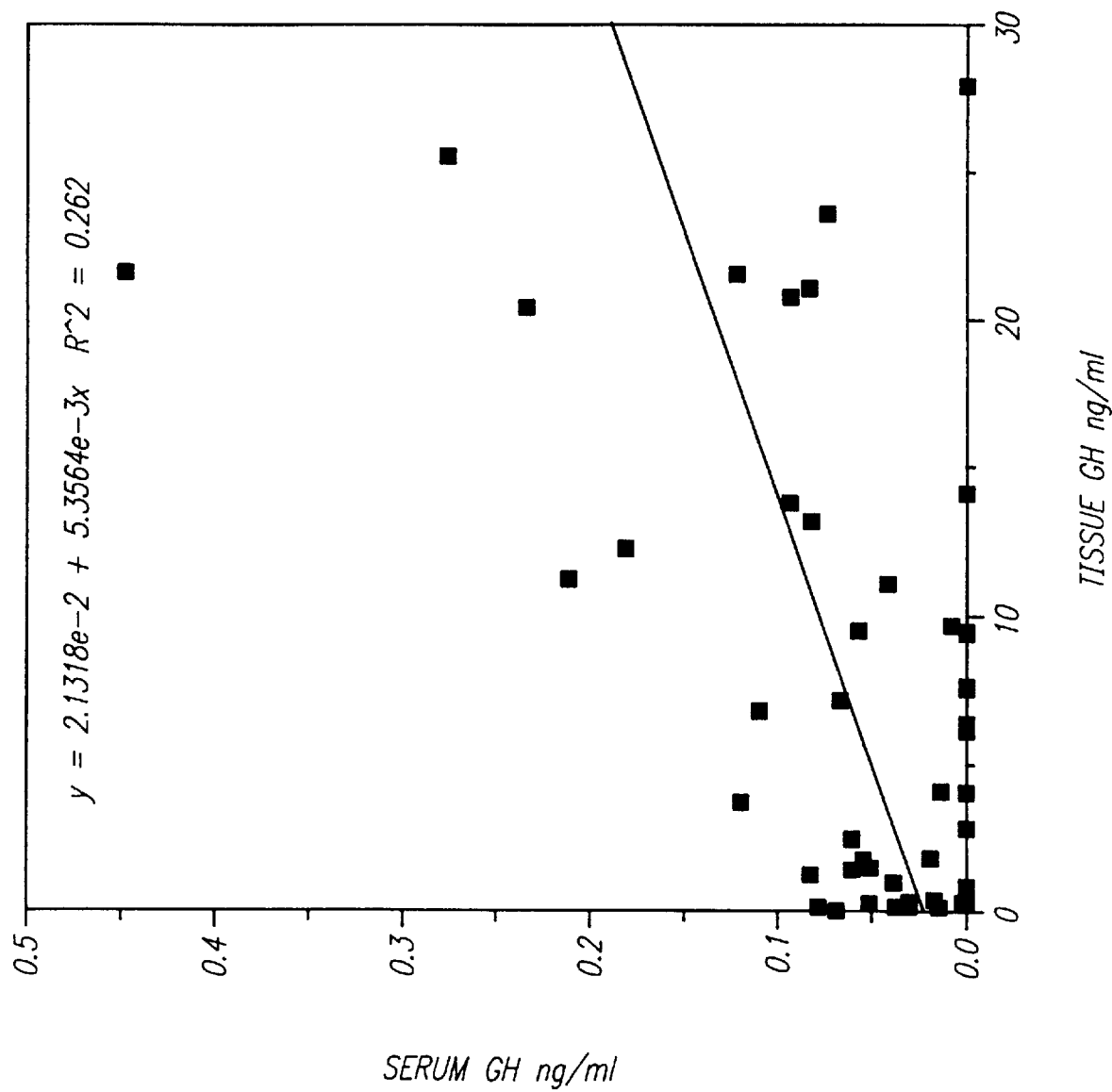
FIG. 9 is a graph showing the correlation between pancreatic tissue expression and serum levels of human growth hormone.

Rats injected with the pFGH.CMV vector expressed higher levels of hGH in the pancreatic tissue (FIG. 7), compared to background levels of pancreatic hGH expression in rats injected with either no DNA (PBS alone) or the pFGH vector (hGH DNA with no promoter). The addition of lipofectin modestly increased hGH expression in rats injected with the pFGH.CMV construct. In addition, rats transfected with the pFGH.CMV vector secreted hGH in the serum at levels increased relative to hGH secretion levels in rats injected with either control samples (no DNA or pFGH, or with samples containing hGH DNA linked to either the chymotrypsin B or RSV promoters (FIG. 8). In FIG. 9, all data from the above experiments (including all controls and vectors) are analyzed by plotting the hGH serum levels against the hGH tissue levels. This graph shows that higher tissue levels result in higher levels of secretion into the blood. Thus, retrograde pancreatic injection of the pFGH-.CMV vector successfully transfected pancreatic cells to provide both hGH pancreatic tissue expression and hGH secretion into the bloodstream.

Example 10

In vivo Gene Transfer of DNA Encoding Intrinsic Factor by Cannulation of Naked DNA into the Pancreas DNA encoding intrinsic factor (Hewitt et al. *Genomics* 10:432–440, 1991) is operably linked to the pancreatic α-amylase promoter. This promoter-intrinsic factor DNA cassette is then inserted into a plasmid capable of replicating in *Escherichia coli*. The plasmid construct is then used to transform *E. coli*, the transformed cells are expanded, and the construct DNA purified. The purified DNA is then resuspended in 0.9% saline and a volume of the DNA solution is administered to a human patient suffering from pernicious anemia. Approximately 100 mg to 200 mg of DNA is delivered to the pancreas of the patient by cannulation of the pancreatic duct by duodenal intubation using endoscopic retrograde cholangio-pancreatography. Expression and secretion of intrinsic factor into the gastrointestinal tract is assessed using the protocol described above. The efficacy of the therapy is also assessed by examining the level of vitamin $B_{12}$ in the patient's blood.

Example 11

In vivo Gene Transfer of DNA Encoding Human Growth Hormone by Cannulation of Naked DNA into the Pancreas DNA encoding human growth hormone (Marshall et al., *Biotechnology* 24:293–298, 1992) is operably linked to the human insulin promoter. This promoter-human growth hormone DNA cassette is then inserted into a plasmid capable of replicating in *Escherichia coli*. The plasmid construct is then used to transform *E. coli*, the transformed cells are expanded, and the construct DNA purified. The purified DNA is then resuspended in 0.9% saline and a volume of the DNA solution is administered to a human patient. Approximately 100 mg to 200 mg of DNA is delivered to the pancreas of the patient by cannulation of the pancreatic duct by duodenal intubation using endoscopic retrograde cholangio-pancreatography. Expression and secretion of human growth hormone into the blood stream is assessed by detection of the protein in the patient's blood.

Example 12

In vivo Gene Transfer of DNA Encoding Human Insulin by Cannulation of Naked DNA into the Pancreas DNA encoding human insulin is operably linked to the pancreatic α-amylase promoter. This promoter-human insulin DNA cassette is then inserted into a plasmid capable of replicating an *Escherichia coli*. The plasmid construct is then used to transform *E. coli*, the transformed cells are expanded, and the construct DNA purified. The purified DNA is then resuspended in 0.9% saline and a volume of the DNA solution is administered to a human patient suffering from an insulin deficiency (e.g., diabetes). Approximately 100 mg to 200 mg of DNA is delivered to the pancreas of the patient by cannulation of the pancreatic duct by duodenal intubation using endoscopic retrograde cholangio-pancreatography. Expression and secretion of insulin into the blood stream is assessed by examining blood glucose levels or by measuring insulin (e.g., by using a human insulin radioimmunoassay kit.

Following procedures similar to those described above, other therapeutic proteins can be expressed from DNA inserted in the genome of a salivary gland cell by gene transfer according to the invention.

The invention now being fully described, it will be apparent to one of ordinary skill in the art that many changes and modifications can be made thereto without departing from the spirit or scope of the appended claims.

What is claimed is:

1. A method of delivering a protein to the bloodstream of a mammal, the method comprising the step of:

introducing a DNA construct into a salivary gland cell in vivo, wherein the DNA construct comprises a DNA sequence of interest which encodes a protein and a eukaryotic promoting sequence operably linked to the DNA sequence of interest;

wherein the introduced DNA construct is expressed and therotein encoded by the introduced DNA construct is delivered into the blood stream of the mammal.

2. The method of claim 1, wherein the salivary gland is a parotid gland or a submandibular gland.

3. The method of claim 1, wherein the mammal is a human and the protein is a human protein.

4. The method of claim 3, wherein the human protein is selected from the group consisting of human growth hormone and human insulin.

5. The method of claim 1, wherein said introducing is by delivery of the DNA construct into a lumen of a salivary gland duct.

6. The method of claim 1, wherein the DNA construct is not contained within a viral particle.

7. The method of claim 1, wherein said introducing is by delivery of the DNA construct into a lumen of a salivary gland duct, and the DNA construct is not contained within a viral particle.

8. The method of claim 1, wherein the protein is insulin.

9. The method of claim 1, wherein the protein is growth hormone.

10. The method of claim 1, wherein the protein is clotting factor VIII.

11. The method of claim 1, wherein the protein is erythropoietin.

* * * * *